United States Patent [19]

Davis et al.

[11] Patent Number: 5,292,747
[45] Date of Patent: Mar. 8, 1994

[54] SUBSTITUTED PYRROLES

[75] Inventors: Peter D. Davis, Letchworth; Christopher H. Hill, Knebworth; Goeffrey Lawton, Hitchin, all of England

[73] Assignee: Hoffman-La Roche Inc., Nutley, N.J.

[21] Appl. No.: 949,185

[22] Filed: Sep. 21, 1992

Related U.S. Application Data

[63] Continuation of Ser. No. 740,546, Aug. 5, 1991, abandoned.

[30] Foreign Application Priority Data

Aug. 7, 1990 [GB] United Kingdom ............. 9017269
May 8, 1991 [GB] United Kingdom ............. 9109959

[51] Int. Cl.$^5$ .................. A61K 31/44; C07D 471/00
[52] U.S. Cl. .................. 514/285; 514/278; 546/18; 546/70
[58] Field of Search ............ 546/18, 70, 18, 70; 514/278, 285, ; A61K 31/44

[56] References Cited

U.S. PATENT DOCUMENTS

4,107,297  8/1978  Omura et al. ............. 514/415
5,057,614 10/1991  Davis et al. ............. 514/415

FOREIGN PATENT DOCUMENTS

9050033   8/1990  Australia .
9054666  11/1990  Australia .
238011A   9/1987  European Pat. Off. .
296110A  12/1988  European Pat. Off. .
0328026   6/1989  European Pat. Off. .
384349    8/1990  European Pat. Off. .
0397060  11/1990  European Pat. Off. .

OTHER PUBLICATIONS

Chem. Abstr. col. 113, No. 11 97381n Sep. 10, 1990.
Tetrahedron Lett. 1990 31(16), 2353–6, David Peter D.
Chem. Abstr. 114(23) 228726z (1990).
Chem. Abstr. 112(11) 98378h (1989).
Chem Abstr. vol. 93 p. 503, 1980, 66027r.
Chem. Abstr. vol. 98 p. 585, 1983, 215863t.
Chem. Abstr. 104: 207579g vol. 104 p. 789, 1986.
Chem. Abstr. 101:55460j vol. 101 p. 654 1984.
Chem. Abstr. 102:6236c vol. 102 p. 567, 1985.
Chem. Abstr. 113:40560r (1990).
Chem Abstr. 114:81582p (1990).
Tetrahedron 47 (26) 4645–64 (1991).

Primary Examiner—Cecilia Tsang
Attorney, Agent, or Firm—George M. Gould; George W. Johnston; Ellen Ciambrone Coletti

[57] ABSTRACT

Compounds of the formula wherein $R^1$, $R^2$, $R^3$, $R^4$, $R^5$, $R^6$, $R^7$, X, m, n, p, and q are as set forth in the specification, as well as pharmaceutically acceptable salts of acidic compounds of formula I with bases and of basic compounds of formula I with acids, which are useful in the control or prevention of inflammatory, immunological, oncological, bronchopulmonary, dermatological or cardiovascular disorders or for the treatment of asthma, AIDS or diabetic complications or for the stimulation of hair growth are described.

24 Claims, No Drawings

SUBSTITUTED PYRROLES

This is a continuation of application Ser. No. 07/740,546 filed Aug. 5, 1991 now abandoned.

BRIEF SUMMARY OF THE INVENTION

The present invention relates to substituted pyrroles of the formula

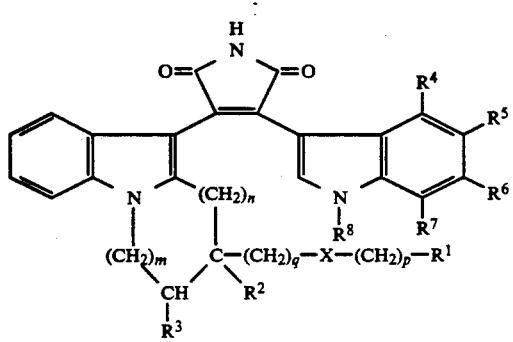

wherein $R^1$ and $R^3$ together form a bond and $R^2$ is hydrogen or $R^1$ and $R^2$ together form a bond and $R^3$ is hydrogen; $R^4$, $R^5$, $R^6$ and $R^7$ each independently are hydrogen, halogen, alkyl, haloalkyl, alkoxy, nitro, amino, alkanoylamino, aroylamino, alkylthio or alkylsulfonyl; $R^8$ is hydrogen, alkyl or aralkyl; X is $-N(R^9)-$ or $-CHN(R^{10},R^{11})-$ in which $R^9$, $R^{10}$ and $R^{11}$ each are hydrogen, alkyl, aralkyl or alkanoyl; m is 0-2 and n is 1-3, with the proviso that the sum of m and n is 1-3; p is 0-4 and q is 0-4, with the proviso that the sum of p and q is 2-4 when X is $-N(R^9)-$, that the sum of p and q is 1-5 when X is $-CHN(R^{10},R^{11})-$ and $R^1$ and $R^2$ together form a bond, that the sum of p and q is 0-4 when X is $-CHN(R^{10},R^{11})-$ and $R^1$ and $R^3$ together form a bond, and that p is 1-4 when X is $-N(R^9)-$, $R^1$ and $R^3$ together represent a bond and m is 0, as well as pharmaceutically acceptable salts of acidic compounds of formula I with bases and of basic compounds of formula I with acids.

DETAILED DESCRIPTION OF THE INVENTION

The present invention relates to substituted pyrroles of the formula

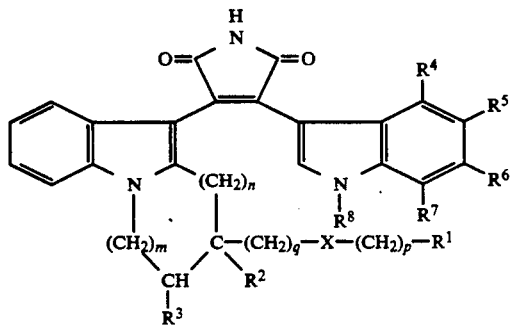

wherein $R^1$ and $R^3$ together form a bond and $R^2$ is hydrogen or $R^1$ and $R^2$ together form a bond and $R^3$ is hydrogen; $R^4$, $R^5$, $R^6$ and $R^7$ each independently are hydrogen, halogen, alkyl, haloalkyl, alkoxy, nitro, amino, alkanoylamino, aroylamino, alkylthio or alkylsulfonyl; $R^8$ is hydrogen, alkyl or aralkyl; X is $-N(R^9)-$ or $-CHN(R^{10},R^{11})-$ in which $R^9$, $R^{10}$ and $R^{11}$ each are hydrogen, alkyl, aralkyl or alkanoyl; m is 0-2 and n is 1-3, with the proviso that the sum of m and n is 1-3; p is 0-4 and q is 0-4, with the proviso that the sum of p and q is 2-4 when X is $-N(R^9)-$, that the sum of p and q is 1-5 when X is $-CHN(R^{10},R^{11})-$ and $R^1$ and $R^2$ together form a bond, that the sum of p and q is 0-4 when X is $-CHN(R^{10},R^{11})-$ and $R^1$ and $R^3$ together form a bond, and that p is 1-4 when X is $-N(R^9)-$, $R^1$ and $R^3$ together represent a bond and m is 0, as well as pharmaceutically acceptable salts of acidic compounds of formula I with bases and of basic compounds of formula I with acids.

Objects of the present invention are the compounds of formula I and their pharmaceutically acceptable salts; a process for making these compounds and salts; novel intermediates useful in the process; medicaments containing the compounds and salts; and the use of the compounds and salts in the control or prevention of illnesses, especially in the control or prevention of inflammatory, immunological, oncological, bronchopulmonary, dermatological and cardiovascular disorders, in the treatment of asthma, AIDS or diabetic complications or for the stimulation of hair growth.

As used herein, the term "alkyl", alone or in combination, denotes a straight-chain or branched-chain alkyl group containing a maximum of 7, preferably a maximum of 4, carbon atoms such as, for example, methyl, ethyl, propyl, isopropyl, butyl, sec.butyl, tert.butyl, pentyl and the like. The term "alkoxy", alone or in combination, denotes an alkyl group as defined earlier which is attached via an oxygen atom, examples of alkoxy groups are methoxy, ethoxy, propoxy, isopropoxy, butoxy, tert.butoxy and the like. A haloalkyl group can carry one or more halogen atoms, with examples of such groups being chloromethyl, trifluoromethyl and the like. The term "alkanoyl", alone or in combination, denotes an alkanoyl group derived from an alkanoic acid containing a maximum of 7, preferably a maximum of 4, carbon atoms, for example, formyl, acetyl, propionyl, butyryl and the like. The term "aralkyl" means an alkyl group as defined earlier in which one of the hydrogen atoms is replaced by a phenyl group or a phenyl group carrying one or more substituents selected from, for example, halogen, alkyl, haloalkyl and hydroxy; such as, for example, benzyl, p-chlorobenzyl, p-tolyl, 2-phenylethyl and the like. The aroyl moiety of an aroylamino group is derived from an aromatic carboxylic acid which can be unsubstituted or substituted with alkyl, alkoxy, halogen and the like, such as, for example, benzoyl, p-toluoyl, p-methoxybenzoyl, o- or p-chlorobenzoyl, 1- or 2-naphthoyl and the like. The term "halogen" denotes fluorine, chlorine, bromine or iodine.

When the compounds of formula I contain a chiral carbon atom they can be present in racemic or optically active form. The present invention includes within its scope not only the racemic compounds, but also the optically active isomers.

One preferred class of compounds of formula I comprises those in which $R^1$ and $R^3$ together form a bond and $R^2$ is hydrogen, X is $-N(R^9)-$ and m, n, p and q each are 1. Another preferred class of compounds of formula I comprises those in which $R^1$ and $R^2$ together form a bond and $R^3$ is hydrogen, X is $-N(R^9)-$, m, n and q each are 1 and p is 2. $R^4$, $R^5$, $R^6$, and $R^7$ each preferably are hydrogen. $R^8$ is alkyl, especially methyl.

$R^9$ is preferably hydrogen or alkyl, especially preferred is hydrogen or methyl. Preferably, $R^{10}$ and $R^{11}$ each represent hydrogen or each represent alkyl, especially methyl.

Other classes of compounds of formula I comprise those in which:

(i) $R^1$ and $R^3$ together form a bond and $R^2$ is hydrogen, Y is —N($R^9$)— and m, n and q are 1 and p is 3;

(ii) $R^1$ and $R^3$ together form a bond and $R^2$ is hydrogen, Y is —CHN($R^{10}$,$R^{11}$)— and m and n each are 1 and p and q each are 0 or m and q each are 0, n is 2 and p is 3;

(iii) $R^1$ and $R^2$ together form a bond and $R^3$ is hydrogen, X is —N($R^9$)— and m, n and q are 1 and p is 3; and (iv) $R^1$ and $R^2$ together form a bond and $R^3$ is hydrogen, X is —CHN($R^{10}$,$R^{11}$)— and m and q each are 0, n is 2 and p is 1 or m and n each are 1, p is 3 and q is 0 or m, n and p each are 1 and q is 0.

Especially preferred compounds of formula I are:

3-[6,7,8,9-Tetrahydrospiro[pyrido[1,2-a]indole-8,3′-pyrrolidin]-10-yl]-4-(1-methyl-3-indolyl)-1H-pyrrole-2,5-dione, cis-3-[2,3,3a,4,11,11a-hexahydro-2-methyl-1H-pyrrolo[3′,4′:4,5]pyrido[1,2-a]indol-10-yl]-4-(1-methyl-3-indolyl)-1H-pyrrole-2,5-dione and trans-3-[2,3,3a,4,11,11a-hexahydro-2-methyl-1H-pyrrolo[3′,4′:4,5]pyrido[1,2-a]indol-10-yl]-4-(1-methyl-3-indolyl)-1H-pyrrole-2,5-dione.

According to the process of the present invention, the compounds of formula I, as well as pharmaceutically acceptable salts of acidic compounds of formula I with bases and of basic compounds of formula I with acids, are prepared by (a) reacting a compound of the formula

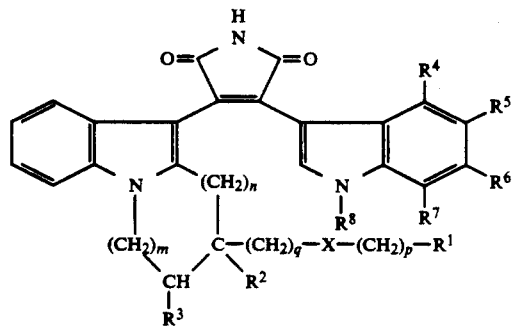

wherein $R^1$, $R^2$, $R^3$, $R^4$, $R^5$, $R^6$, $R^7$, $R^8$, m, n, p and q are described above and X′ is —N($R^{9\prime}$)— or —CHN($R^{10\prime}$,$R^{11\prime}$)— in which $R^{9\prime}$, $R^{10\prime}$ and $R^{11\prime}$ each are hydrogen, alkyl, aralkyl, alkanoyl, alkoxycarbonyl or aryloxycarbonyl, with ammonia under pressure or with hexamethyldisilazane and methanol and, where required, cleaving off any alkoxycarbonyl or aralkoxycarbonyl group(s) present in the reaction product, or (b) for the preparation of a compound of formula I in which $R^8$ is hydrogen, debenzylating a compound of formula I in which $R^8$ is benzyl, and (c) if desired, converting an acidic compound of formula I into a pharmaceutically acceptable salt with a base or converting a basic compound of formula I into a pharmaceutically acceptable salt with an acid.

The alkoxycarbonyl or araloxycarbonyl group which can be present as $R^{9\prime}$, $R^{10\prime}$ or $R^{11\prime}$ in the starting material of formula II is preferably the tert.butyloxycarbonyl or benzyloxycarbonyl group, respectively.

The reaction of a compound of formula II with ammonia under pressure in accordance with embodiment (a) of the process is conveniently carried out using aqueous ammonia, preferably 33% aqueous ammonia, and in the presence of a water-miscible inert organic solvent such as DMF (dimethylformamide). The reaction is preferably carried out at an elevated temperature, for example, at a temperature in the range of from about 100° C. to about 150° C.

The reaction of a compound of formula II with hexamethyldisilazane and methanol, also in accordance with embodiment (a) of the process, is preferably carried out in DMF at about room temperature or in acetonitrile at from about room temperature to about 82° C. However, it can also be carried out in a halogenated hydrocarbon, for example, chloroform, carbon tetrachloride or chlorobenzene, or an aromatic hydrocarbon, for example, benzene, toluene or xylene, and at an elevated temperature, for example, from about 40° C. to 110° C.

The cleavage of any alkoxycarbonyl or aralkoxycarbonyl group(s) which may be present in the reaction product can be carried out in a known manner. For example, the cleavage can be carried out using a mineral acid such as hydrochloric acid in an inert organic solvent such as an ether, for example, THF (tetrahydrofuran) or dioxan; an alkanol, for example, methanol or ethanol, or a halogenated, especially chlorinated, hydrocarbon, for example, methylene chloride, and the like or using trifluoroacetic acid. The cleavage is suitably carried out at a temperature between about 0° C. and room temperature.

The debenzylation of a compound of formula I in which $R^8$ is benzyl, in accordance with embodiment (b) of the process, to give a compound of formula I in which $R^8$ is hydrogen can be carried out in a known manner. Thus, the debenzylation can be carried out using hydrogen in the presence of a suitable catalyst, for example, a palladium catalyst which may be supported on a carrier material such as palladium/charcoal, and in an inert organic solvent, for example, an alkanol, such as, methanol or ethanol, conveniently at ambient temperature and under atmospheric pressure.

The conversion of an acidic compound of formula I into a pharmaceutically acceptable salt in accordance with embodiment (c) of the process can be carried out by treatment with a suitable base in a known manner. Suitable salts are those derived not only from inorganic bases, for example, sodium salts, potassium salts, calcium salts and the like, but also from organic bases, for example ethylenediamine, monoethanolamine, diethanolamine and like salts. The conversion of a basic compound of formula I into a pharmaceutically acceptable salt, also in accordance with embodiment (c) of the process, can be carried out by treatment with a suitable acid in a known manner. Suitable salts are those derived not only from inorganic acids, for example, hydrochlorides, hydrobromides, phosphates, sulphates and the like, but also from organic acids, for example, acetates, citrates, fumarates, tartrates, maleates, methanesulphonates, p-toluenesulphonates and the like.

The compounds of formula II which are used as starting materials in embodiment (a) of the process are novel and also form an object of the present invention. They can be prepared, for example, by reacting a compound of the formula

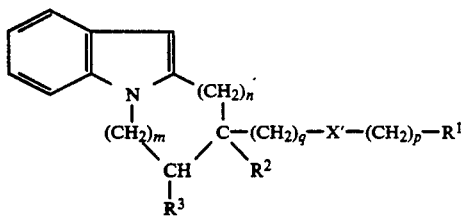
(III)

wherein $R^1$, $R^2$, $R^3$, m, n, p, q and X' are as described above, with oxalyl chloride and reacting the resulting compound of the formula

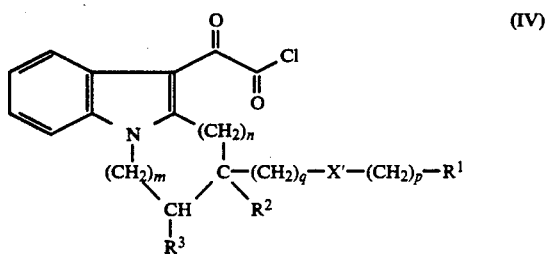
(IV)

wherein $R^1$, $R^2$, $R^3$, m, n, p, q and X' are as defined above, with a compound of the formula

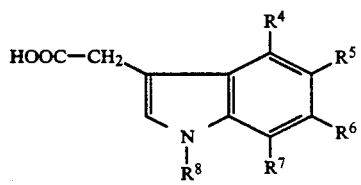
(V)

wherein $R^4$, $R^5$, $R^6$, $R^7$ and $R^8$ are as described above, and, if desired, cleaving off any alkoxycarbonyl or aralkoxycarbonyl group(s) present in the reaction product and, also if desired, alkylating, aralkylating or alkanoylating the product obtained.

The reaction of a compound of formula III with oxalyl chloride is conveniently carried out in an inert organic solvent, such as, a halogenated aliphatic hydrocarbon, for example, dichloromethane and the like, at a temperature between about −78° C. and the reflux temperature of the reaction mixture, preferably at about −78° C. to about 0° C.

The reaction of a compound of formula IV with a compound of formula V is preferably carried out in the presence of an acid-binding agent, expediently a tertiary amine such as a trialkylamine, for example, triethylamine, diisopropylethylamine and the like, and in an inert organic solvent such as a halogenated aliphatic hydrocarbon, for example, dichloromethane and the like, at about room temperature. In a preferred procedure a compound of formula IV is reacted in situ with a compound of formula V.

The optional cleavage of any alkoxycarbonyl or aralkoxycarbonyl group(s) which may be present in the reaction product can be carried out in the same manner to that described earlier in connection with the cleavage of these groups from a reaction product obtained according to embodiment (a) of the process.

The optional alkylation, aralkylation or alkanoylation after the cleavage of any alkoxycarbonyl or aralkoxycarbonyl group(s) can be carried out according to known methods. Suitably, the alkylation or aralkylation is carried out by reductive alkylation or reductive aralkylation.

The compounds of formulas III and V are known compounds or analogs of known compounds which can be prepared in a similar manner to the known compounds. Further, the Examples hereinafter contain detailed information containing the preparation of compounds of formula III.

The compounds of formula I and their pharmaceutically acceptable salts are protein kinase inhibitors. The compounds of formula I and their pharmaceutically acceptable salts inhibit cellular processes, for example, cell proliferation and secretion, and can be used in the control or prevention of illnesses, for example, in the control or prevention of inflammatory disorders, such as, arthritis, immune diseases, psoriasis, contact dermatitis, in conjunction with organ transplants and also in oncology. They inhibit infection of cells with human immunodeficiency virus or Epstein-Barr virus and are thus useful in the treatment of AIDS and infectious mononucleosis. The compounds and salts of the present invention also inhibit smooth muscle contraction and can therefore be used against cardiovascular and bronchopulmonary disorders. Further, they are also useful in asthma therapy. The present compounds and salts also inhibit platelet aggregation and can be used in the control or prevention of thrombosis. Further, they inhibit the release of mediators from activated neutrophils and can therefore be used to control ischemic damage, for example, in the heart or brain. The present compounds and salts inhibit neurotoxicity induced by elevated glucose levels and are thus useful for the treatment of diabetic complications. The present compounds and salts stimulate hair growth and can therefore be used to prevent or repress baldness.

The activity of the present compounds in inhibiting protein kinase C can be demonstrated by means of the in vitro test procedure described in Biochem. and Biophys. Research Comm. 19 (1979) 1218.

The $IC_{50}$ values in the following Table are that concentration of test compound which reduces by 50% the protein kinase-induced incorporation of $^{32}P$ from $[\gamma-^{32}P]ATP$ into histone.

TABLE

| Product of Example No. | $IC_{50}$ (nM) |
|---|---|
| 1 | 40 |
| 6 | 30 |
| 14 | 7 |

The compounds of formula I and their aforementioned salts can be used as medicaments, for example, in the form of pharmaceutical preparations. The pharmaceutical preparations can be administered orally, for example, in the form of tablets, coated tablets, dragees, hard and soft gelatin capsules, solutions, emulsions or suspensions. However, they can also be administered rectally (for example, in the form of suppositories) or parenterally (for example, in the form of injectable solutions).

For the manufacture of pharmaceutical preparations, the compounds of formula I and their aforementioned salts can be formulated with therapeutically inert, inorganic or organic carriers. Lactose, maize starch or derivatives thereof, talc, stearic acid or its salts and the like can be used, for example, as such carriers for tablets, coated tablets, dragees and hard gelatin capsules.

Suitable carriers for soft gelatin capsules are, for example, vegetable oils, waxes, fats, semi-solid and liquid polyols and the like. Depending on the nature of the active substance no carriers are, however, generally required in the case of soft gelatine capsules. Suitable carriers for the manufacture of solutions and syrups are, for example, water, polyols, saccharose, invert sugar, glucose and the like. Suitable carriers for injectable solutions are, for example, water, alcohols, polyols, glycerine, vegetable oils and the like. Suitable carriers for suppositories are, for example, natural or hardened oils, waxes, fats, semi-liquid polyols and the like.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain still other therapeutically valuable substances. Pharmaceutical compositions containing a compound of formula I or a salt thereof as defined above and a therapeutically inert carrier are also objects of the present invention.

As mentioned above, the compounds of formula I and their aforementioned salts can be used in the control or prevention of illnesses, especially in the control or prevention of inflammatory, immunological, bronchopulmonary, dermatological and cardiovascular disorders, for the treatment of asthma, AIDS or diabetic complications or for the stimulation of hair growth. The dosage can vary within wide limits and will, of course, be adjusted to the individual requirements in each particular case. In general, in the case of oral administration to adults, a daily dosage of about 5 mg to about 500 mg should be appropriate, although the upper limit may be exceeded when this is found to be indicated. The daily dosage can be administered as a single dose or in divided doses.

EXAMPLE 1

(A) A mixture of 4.09 g of 1,1,1,3,3,3-hexamethyldisilazane and 0.41 g of methanol was added to a solution of 1.40 g of 3-[1'-(tert.butoxycarbonyl)-7,9-dihydrospiro[pyrido[1,2-a]indole-8(6H),3'-pyrrolidin]-10-yl]-4-(1-methyl-3-indolyl)furan-2,5-dione in 25 ml of dry DMF and stirred for 16 hours. The mixture was poured into 100 ml of water and extracted with ethyl acetate. The ethyl acetate extracts were washed with sodium chloride solution, dried and concentrated. There were obtained 820 mg of 3-[1'-(tert.butoxycarbonyl)-7,9-dihydrospiro[pyrido-[1,2-a]indole-8(6H).3'-pyrrolidin]-10-yl]-4-(1-methyl-3-indolyl)-1H-pyrrole-2,5-dione after chromatography on silica gel using dichloromethane/methanol (9:1) for the elution.

(B) A solution of 780 mg of the product of (A) in 100 ml of dichloromethane was treated at 0° C. with 5 ml of trifluoroacetic acid and the mixture was stirred for 2 hours. The solvent was removed under reduced pressure and the residue was chromatographed on silica gel using chloroform/methanol/acetic acid/water (60:18:2:3) for the elution. There were obtained 145 mg of 3-[6,7,8,9-tetrahydrospiro[pyrido[1,2-a]indole-8,3'-pyrrolidin-10-yl]-4-(1-methyl-3-indolyl)-pyrrole-2,5-dione trifluoroacetate of melting point 177°-180° C.

The furandione starting material was prepared as follows:

(i) 1.3 g of sodium hydride were added over 0.5 hour to a stirred, ice-cold solution of 12.85 g of ethyl 6,7-dihydro-9-hydroxypyrido[1,2-a]indole-8-carboxylate in 200 ml of DMF and the mixture was stirred for a further 0.5 hour. A solution of 9.2 g of ethyl bromoacetate in 50 ml of DMF was added dropwise to the cooled mixture. After a further 3 hours at room temperature the mixture was poured into 1.5 l of water and extracted with diethyl ether. The ethereal extracts were washed with water, dried and concentrated to give 16.3 g of ethyl 8-(ethoxycarbonyl)-6,7,8,9-tetrahydro-9-oxopyrido[1,2-a]indole-8-acetate.

(ii) A solution of 4.2 g of the product of (i) in 100 ml of ethanol was treated with a suspension of Raney nickel in water and the mixture was heated at reflux for 4 hours. The cooled mixture was filtered and the residue was washed with ethyl acetate. The filtrate was extracted with ethyl acetate. The ethyl acetate solution was dried and the solvent was removed under reduced pressure to give 3.0 g of ethyl 8-(ethoxycarbonyl)-6,7,8,9-tetrahydropyrido[1,2-a]indole-8-acetate.

(iii) 3.0 g of the product of (ii) were added to a solution of 1.4 g of sodium hydroxide in 100 ml of ethanol and the mixture was heated under reflux for 2 hours. The cooled mixture was filtered and the residue was dissolved in 100 ml of water and acidified with 2M hydrochloric acid. The resulting precipitate was filtered off, washed with water and dried. There were obtained 1.7 g of 8-carboxy-6,7,8,9-tetrahydropyrido[1,2-a]indole-8-acetic acid.

(iv) A mixture of 100 mg of 8-carboxy-6,7,8,9-tetrahydropyrido[1,2-a]indole-8-acetic acid and 69 mg of ammonium carbonate was heated at 200° C. for 1 hour. After cooling and chromatography on silica gel using dichloromethane/methanol (9:1) for the elution there were obtained 64 mg of 7,9-dihydrospiro[pyrido[1,2-a]indole-8(6H),3'-pyrrolidine]-2',5'-dione.

(v) A solution of 100 mg of 7,9-dihydrospiro[pyrido[1,2-a]indole-8(6H),3'-pyrrolidine]-2',5'-dione in 10 ml of THF was added dropwise to a suspension of 152 mg of lithium aluminium hydride in 20 ml of THF. After completion of the addition the mixture was heated at reflux for 20 hours. 20 ml of water were added to the cooled mixture and the resulting mixture was extracted with diethyl ether. The etheral extracts were washed with water, dried and concentrated. There were obtained 62 mg of 7,9-dihydrospiro[pyrido[1,2-a]indole-8(6H),3'-pyrrolidine].

(vi) A solution of 680 mg of 7,9-dihydrospiro[pyrido[1,2-a]indole-8(6H),3'-pyrrolidine] in 20 ml of dichloromethane was added dropwise to an ice-cold solution of 660 mg of di-tert.butyl dicarbonate and 300 mg of triethylamine in 25 ml of dichloromethane. After completion of the addition the mixture was stirred for 16 hours and washed in succession with dilute hydrochloric acid, saturated aqueous sodium bicarbonate solution and water. The organic phase was dried and concentrated to give a gum which, upon trituration with n-hexane, gave 711 mg of 1'-(tert.butoxycarbonyl)-7,9-dihydrospiro[pyrido[1,2-a]indole-8(6H),3'-pyrrolidine].

(vii) 300 mg of oxalyl chloride were added dropwise to a solution of 700 mg of the product of (vi) in 50 ml of dichloromethane at 0° C. After 4 hours, the solvent was removed under reduced pressure and the residue was dissolved in 50 ml of dichloromethane. The solution was added dropwise to a solution of 450 mg of 1-methylindole-3-acetic acid and 540 mg of triethylamine in 50 ml of dichloromethane. After 48 hours, the mixture was concentrated and the residue was chromatographed on silica gel using dichloromethane/methanol (95:5) for the elution. There were obtained 370 mg of 3-[1'-(tert.butoxycarbonyl)-7,9-dihydrospiro[-pyrido[1,2-a]indole-8(6H),3'-pyrrolidin]-10-yl]-4-(1-methyl-3-indolyl)furan-2,5-dione.

EXAMPLE 2

(A) A mixture of 1.08 g of 1,1,1,3,3,3-hexamethyldisilazane and 0.11 g of methanol was added to a solution of 380 mg of 3-[1-(tert.butoxycarbonyl)-7',9'-dihydrospiro[piperidine-3,8'(6'H)-pyrido[1,2-a]indol]-10'-yl]-4-(1-methyl-3-indolyl)furan-2,5-dione in 10 ml of DMF and the mixtue was stirred for 16 hours and subsequently poured into 50 ml of water. The resulting mixture was extracted with dichloromethane and the extracts were washed with sodium chloride solution, dried and concentrated. Chromatography of the residue on silica gel using dichloromethane/methanol (9:1) for the elution gave 220 mg of 3-[1-(tert.butoxycarbonyl)-7',9'-dihydrospiro[piperidine-3,8'(6'H)-pyrido[1,2-a]indol]-10'-yl]-4-(1-methyl-3-indolyl)-1H-pyrrole-2,5-dione.

(B) In a manner analogous to that described in Example 1(B), from 150 mg of the product of Example 2(A) and 1 ml of trifluoroacetic acid there were obtained 25 mg of 3-[7',9'-dihydrospiro-[piperidine-3,8'(6'H)-pyrido[1,2-a]indol]-10'-yl]-4-(1-methyl-3-indolyl)-1H-pyrrole-2,5-dione trifluoroacetate of melting point 172° C.

The furandione starting material was prepared as follows:

(i) A mixture of 5 g of ethyl 6,7-dihydro-9-hydroxypyrido[1,2-a]indole-8-carboxylate. 1.85 g of methyl acrylate and 250 mg of 1,1,3,3-tetramethylguanidine was dissolved in 250 ml of acetonitrile and the solution was stirred overnight, poured into 500 ml of water containing 20 ml of 2M hydrochloric acid and extracted with diethyl ether. The ethereal extracts were washed with water, dried and concentrated. There were obtained 6.33 g of methyl 8-(ethoxycarbonyl)-6,7,8,9-tetrahydro-9-oxopyrido[1,2-a]indole-8-propionate.

(ii) 4.0 g of the product of (i) were dissolved in 100 ml of ethanol and treated with a suspension of Raney nickel in water. After heating under reflux for 4 hours, the mixture was cooled and filtered, and the residue was washed with ethyl acetate. The filtrate was extracted with ethyl acetate and the extracts and washings were dried and concentrated. 3.3 g of methyl 8-(ethoxycarbonyl)-6,7,8,9-tetrahydro-9-pyrido[1,2-a]indole-8-propionate were obtained.

(iii) 3.2 g of the product of (ii) were added to a solution of 1.55 g of sodium hydroxide in 100 ml of ethanol and the mixture was heated at reflux for 2 hours. The cooled mixture was filtered and the residue was dissolved in 100 ml of water and acidified with 2N hydrochloric acid. The resulting precipitate was filtered off, washed with water and dried. There were obtained 2.2 g of 8-carboxy-6,7,8,9-tetra-hydropyrido[1,2-a]indole-8-propionic acid.

(iv) A mixture of 2.2 g of the product of (iii) and 1.44 g of ammonium carbonate was heated at 200° C. for 3 hours, cooled and then chromatographed on silica gel using dichloromethane/methanol (9:1) for the elution to give 610 mg of 7',9'-dihydrospiro[piperdine-3,8'(6'H)-pyrido[1.2-a]indole]-2,6-dione.

(v) A solution of 610 mg of the product of (iv) in 10 ml of THF was added dropwise to a suspension of 0.865 g of lithium aluminium hydride in 20 ml of THF. After completion of the addition, the mixture was heated at reflux for 20 hours. 20 ml of water were added slowly to the cooled mixture and the resulting mixture was extracted with diethyl ether. The ethereal extracts were washed with water, dried and concentrated. There were obtained 456 mg of 7',9'-dihydrospiro[piperidine-3,8'(6'H)-pyrido[1,2-a]indole].

(vi) A solution. of 456 mg of the product of (v) in 25 ml of dichloromethane was added dropwise to an ice-cold solution of 415 mg of di-tert.butyl dicarbonate and 192 mg of triethylamine in 25 ml of dichloromethane. After completion of the addition, the mixture was stirred for 16 hours and washed in succession with dilute hydrochloric acid, saturated aqueous sodium bicarbonate solution and water. The organic phase was dried and concentrated. These were obtained 611 mg of 1-(tert.butoxycarbonyl)-7',9'-dihydrospiro[piperidine-3,8'(6'H)-pyrido[1,2-a]indole].

(vii) 251 mg of oxalyl chloride were added dropwise to a solution of 611 mg of the product of (vi) in 50 ml of dichloromethane at 0° C. After 4 hours, the solvent was removed under reduced pressure and the residue was dissolved in 50 ml of dichloromethane. The resulting solution was added dropwise to a solution of 374 mg of 1-methylindole-3-acetic acid and 454 mg of triethylamine in 50 ml of dichloromethane. After 48 hours, the mixture was concentrated and the residue was chromatographed on silica gel using dichloromethane/methanol (95:5) for the elution. There were obtained 394 mg of 3-[1-(tert.butoxycarbonyl)-7',9'-dihydrospiro[-piperidine-3,8'(6'H)-pyrido[1,2-a]-indol]-10'-yl]-4-(1-methyl-3-indolyl)furan-2,5-dione.

EXAMPLE 3

(A) A solution of 150 mg of cis-3-[2-(tert.butoxyformamido)-8',9'-dihydrospiro[cyclopropane-1,7'(6'H)-pyrido-[1,2-a]indol]-10-yl]-4-(1-methyl-3-indolyl)furan-2,5-dione in 5 ml of DMF and 5 ml of 33% aqueous ammonia was heated at 100° C. for 1 hour in a sealed vessel. The cooled reaction mixture was extracted with ethyl acetate and the organic extracts were washed with water, dried and evaporated. Crystallization of the residue from ethyl acetate/n-hexane gave 120 mg of cis-3-[2-(tert.butoxyformamido)-8',9'-dihydrospiro[cyclopropane-1,7'(6'H)-pyrido[1,2a-]indol]-10-yl]-4-(1-methyl-3-indolyl)-1H-pyrrole-2,5-dione of melting point 225°-228° C.

(B) 110 mg of the product of (A) were dissolved in 25 ml of a saturated solution of hydrogen chloride in ethyl acetate. The resulting solution was left to stand at room temperature for 18 hours and the solid which formed was filtered off to give 80 mg of cis-3-[2-amino-8', 9'-dihydrospiro[cyclopropane-1,7'(6'H)-pyrido[1,2-a]indol]-10-yl]-4-(1-methyl-3-indolyl)-1H-pyrrole-2,5-dione hydrochloride of melting point 288°-289° C. (decomposition).

The furandione starting material was prepared as follows:

(i) 720 mg of a 60% suspension of sodium hydride in mineral oil and 3.96 g of trimethylsulphoxonium iodide were dissolved in 60 ml of DMSO (dimethyl sulphoxide). The mixture was stirred at room temperature for 45 minutes under a nitrogen atmosphere. A solution of 2.8 g of 8,9-dihydropyrido[1,2-a]indol-7(6H)-one in 15 ml of DMSO was added and the solution obtained was stirred for 0.5 hour. The mixture was poured into 300 ml of water and extracted with ethyl acetate. The organic extracts were washed with water, dried and evaporated under reduced pressure to give 2.6 g of a solid. A sample was triturated with n-hexane to give 8',9'-dihydrospiro[oxirane-2,7'(6'H)-pyrido[1,2-a]indole] of melting point 104°–107° C.

(ii) A stirred solution of 6.27 g of triethylphosphonoacetate in 120 ml of dimethoxyethane was treated at room temperature under a nitrogen atmosphere with 1.12 g of a 60% suspension of sodium hydride in mineral oil. After 15 minutes, the solution obtained was treated with a solution of 2.8 g of the product of (i) in 20 ml of dimethoxyethane. The mixture was then heated to reflux for 20 hours. The cooled mixture was poured into 300 ml of saturated ammonium chloride solution and the product was extracted with ethyl acetate. The organic extracts were washed with sodium chloride solution, dried and evaporated to give an oil which was purified by chromatography on silica gel using diethyl ether/n-hexane (1:3) for the elution. 2.05 g of ethyl 8',9'-dihydrospiro[cyclopropane-1,7'(6'H)-pyrido[1,2-a]indole]-2-carboxylate were obtained.

(iii) A solution of 2.0 g of the product of (ii) in 90 ml of ethanol was treated with a solution of 1.12 g of potassium hydroxide in 10 ml of water. The solution obtained was stirred for 6 hours and then poured into 100 ml of 2M hydrochloric acid and the product was extracted with ethyl acetate. The organic extracts were washed with sodium chloride solution, dried and evaporated to give 1.74 g of 8',9'-dihydrospiro[cyclopropane-1,7'(6'H)-pyrido[1,2-a]indole]-2-carboxylic acid.

(iv) 1.16 g of the product of (iii) in 25 ml of acetone and 1 ml of water were cooled in an ice/salt bath. 586 mg of triethylamine and 678 mg of ethyl chloroformate were then added and the resulting solution was stirred for 0.5 hour. 406 mg of sodium azide were then added and the mixture was stirred at 0° C. for 1 hour. The acetone was removed by evaporation and the residue was extracted with ethyl acetate. The organic extract was dried and evaporated. The residue was purified by chromatography on silica gel using diethyl ether/n-hexane (1:2) for the elution to give 980 mg of an oil. This oil was heated to 100° C. in 25 ml of toluene for 2 hours. The solvent was removed by evaporation to give 800 mg of 8',9'-dihydrospiro-[cyclopropane-1,7'(6'H)-pyrido[1,2-a]indol]-2-yl isocyanate.

(v) A solution of 800 mg of the isocyanate of (iv) in 50 ml of dioxan was heated to 60° C. for 2 hours with 5 ml of 2M hydrochloric acid and then at reflux for 1 hour. The solvent was removed under reduced pressure and the residue was partitioned between ethyl acetate and 2M sodium hydroxide solution. The organic extracts were washed with water, dried and evaporated. The obtained oil was purified by chromatography on silica gel using methanol/dichloromethane (1:19) for the elution, there being obtained 345 mg of cis-8',9'-dihydrospiro[cyclopropane-1,7'(6'H)-pyrido[1,2-a]indole]-2-amine and 90 mg of trans-8',9'-dihydrospiro[cyclopropane-1,7'(6'H)-pyrido-[1,2-a]indole]-2-amine.

(vi) A solution of 370 mg of the product of (v) in 30 ml of dichloromethane was treated at 0° C. under a nitrogen atmosphere with 225 mg of triethylamine and 415 mg of di-tert.butyl dicarbonate. The solution obtained was stirred at 0° C. for 3 hours and then at room temperature for 18 hours. The solvent was removed by evaporation and the residue was purified by chromatography on silica gel using diethyl ether/n-hexane (1:1) for the elution. Crystallization of the product from diethyl ether/n-hexane gave 330 mg of tert.butyl cis-8',9'-dihydrospiro[cyclopropane-1,7'(6'H)-pyrido-[1,2-a]indol]-2-ylcarbamate of melting point 114°–116° C.

(vii) 152 mg of oxalyl chloride were added to a solution of 310 mg of the product of (vi) in 30 ml of diethyl ether under a nitrogen atmosphere. After 15 minutes, the solvent was removed under reduced pressure and the residue was dissolved in 30 ml of dichloromethane. 227 mg of 1-methyl-3-indolylacetic acid and 240 mg of triethylamine were added to the solution and the solution obtained was stirred for 72 hours. The solvent was removed by evaporation and the residue was purified by chromatography on silica gel using ethyl acetate/n-hexane (1:1) for the elution. Crystallization from ethyl acetate gave 160 mg of cis-3-[2-(tert.-butoxyformamido)-8',9'-dihydrospiro[cyclopropane-1,7'(6'H)-pyrido[1,2-a]indol]-10-yl]-4-(1-methyl-3-indolyl)-furan-2,5-dione of melting point 210°–213° C.

EXAMPLE 4

(A) A solution of 90 mg of trans-3-[2-(tert.-butoxyformamido)-8',9'-dihydrospiro[cyclopropane-1,7'(6'H)-pyrido[1,2-a]indol]-10-yl]-4-(1-methyl-3-indolyl)furan-2,5-dione in 5 ml of DMF and 5 ml of 33% aqueous ammonia was heated to 100° C. for 1 hour in a sealed vessel. The cooled mixture was extracted with ethyl acetate and the organic extracts were washed with water, dried and evaporated to dryness. Crystallization of the residue from ethyl acetate gave 70 mg of trans-3-[2-(tert.-butoxyformamido)-8',9'-dihydrospiro[cyclopropane-1,7'(6'H)-pyrido[1,2-a]indol]-10-yl]-4-(1-methyl-3-indolyl)-1H-pyrrole-2,5-dione of melting point 250°–250° C.

(B) 65 mg of the product of (A) were dissolved in 25 ml of a saturated solution of hydrogen chloride in ethyl acetate. The resulting solution was left to stand at room temperature for 18 hours and the solid formed was filtered off to give 45 mg of trans-3-[2-amino-8',9'-dihydrospiro[cyclopropane-1,7'(6'H)-pyrido[1,2-a]indol]-10-yl]-4-(1-methyl-3-indolyl)-1H-pyrrole-2,5-dione hydrochloride in the form of an orange colored solid of melting point 260°–264° C. (decomposition).

The furandione starting material was prepared as follows:

(i) A solution of 180 mg of trans-8',9'-dihydro-spiro[-cyclopropane-1,7'(6'H)-pyrido[1,2-a]indole]-2-amine [prepared as described in Example 3(v)] in 25 ml of dichloromethane was treated at 0° C. under a nitrogen atmosphere with 110 mg of triethylamine and 230 mg of di-tert.butyl dicarbonate. The solution obtained was stirred at 0° C. for 3 hours and then at room temperature for 3 hours. The solvent was removed by evaporation and the residue was purified by chromatography on silica gel using diethyl ether/n-hexane (1:1) for the elution. Crystallization of the product from diethyl ether/n-hexane gave 190 mg of tert.butyl trans-8',9'-dihydrospiro[cyclopropane-1,7'(6'H)-pyrido[1,2a]indol]-2-ylcarbamate of melting point 154°–156° C.

(ii) 90 mg of oxalyl chloride were added to a solution of 180 mg of the product of (i) in 20 ml of diethyl ether under a nitrogen atmosphere. After stirring for 15 minutes, the solvent was removed under reduced pressure and the residue was dissolved in 20 ml of dichloromethane. 132 mg of 1-methyl-3-indolylacetic acid and 142 mg of triethylamine were added and the solution obtained was stirred for 72 hours. The solvent was removed by evaporation and the residue was purified by chromatography on silica gel using ethyl acetate/n-hexane (1:1) for the elution. Crystallization from ethyl acetate gave 100 mg of trans-3-[2-(tert-butoxyformamido)-8',9'-dihydrospiro[cyclopropane-1,7'(6'H)-pyrido[1,2- a]indol]-10-yl]-4-(1-methyl-3-indolyl)-furan-2,5-dione of melting point 187°–193° C.

EXAMPLE 5

(A) A solution of 700 mg of cis-3-[2-(tert.butoxy-carbonyl)-2,3,3a,4,11,11a-hexahydro-1H-pyrrolo[3',4':4,5-]pyrido[1,2-a]indol-10-yl]-4-(1-methyl-3-indolyl)furan-2,5-dione in 6 ml of DMF and 6 ml of 33% aqueous ammonia was heated to 100° C. for 2.5 hours in a sealed vessel. The mixture was left to cool and the solid formed was filtered off and dried to give 400 mg of cis-3-[2-(tert.butoxycarbonyl)-2,3,3a,4, 11,11a-hexahydro-1H-pyrrolo[3',4':4,5]pyrido[1,2-a]-indol-10-yl]-4-(1-methyl-3-indolyl)-1H-pyrrole-2,5-dione of melting point 173°–175° C.

(B) A stirred solution of 400 mg of the product of (A) in 15 ml of dichloromethane was treated with 3 ml of trifluoroacetic acid. After 0.5 hour the solvent was removed under reduced pressure and the residue was triturated with 10 ml of methanol to give 270 mg of cis-3-[2,3,3a,4,11, 11a-hexahydro-1H-pyrrolo[3',4':4,5-]pyrido[1,2-a]indol-10-yl]-4-(1-methyl-3-indolyl)-1H-pyrrole-2,5-dione trifluoroacetate of melting point 268°–269° C.

The furandione starting material was prepared as follows:

(i) 200 ml of a 2M solution of lithium borohydride in THF were added dropwise to a stirred solution of 100 g of methyl 1-benzyl-5-oxo-3-pyrrolidinecarboxylate in 600 ml of THF under a nitrogen atmosphere. After 3 hours, the mixture was cooled to 10° C. and treated with 200 ml of 50% aqueous acetic acid. The solvents were removed under reduced pressure and the residue was partitioned between dichloromethane and saturated sodium bicarbonate solution. The organic extracts were dried and evaporated to dryness to give 92 g of 1-benzyl-4-(hydroxymethyl)-2-pyrrolidinone. This was dissolved in 200 ml of pyridine and the solution was treated with 95 g p-toluenesulphonyl chloride. The solution obtained was stirred for 18 hours and then concentrated. The residue was partitioned between dichloromethane and 2M hydrochloric acid. The organic phase was washed with water, dried and evaporated to dryness. Crystallization of the residue from diethyl ether/n-hexane gave 115 g of 1-benzyl-4-(p-toluenesulphonyloxy)-2-pyrrolidinone of melting point 83°–84° C.

(ii) A solution of 66.2 g of ethyl indole-2-carboxylate in 350 ml of DMF was added to a suspension of 12 g of sodium hydride (80% dispersion in mineral oil) in 80 ml of DMF. After stirring for 0.5 hour under a nitrogen atmosphere the solution obtained was treated with a solution of 115 g of 1-benzyl-4-(p-toluenesulphonyloxy)-2-pyrrolidinone in 500 ml of DMF. After completion of the addition the mixture was heated to 60° C. for 0.75 hour and then at 70° C. for 1 hour. The solution obtained was cooled in an ice bath and treated with water and 2M hydrochloric acid. After stirring for 15 minutes the precipitate formed was filtered off and dried to give 96.2 g of ethyl 1-[(1-benzyl-5-oxo-3-pyrrolidinyl)methyl]-2-indolecarboxylate of melting point 93°–94° C.

(iii) A solution of 95 g of the product of (ii) in 400 ml of THF was added to a stirred solution of 30.3 of potassium tert.butoxide in 1500 ml of THF under a nitrogen atmosphere. The mixture was stirred for 1.5 hours and then cooled to 10° C. and treated with 300 ml of 1M hydrochloric acid. The precipitate formed was filtered off and dried, and the filtrate was concentrated to give a further precipitate. This precipitate was filtered off, dried and combined with the initially obtained precipitate to give a total of 54.6 g of 2-benzyl-3,3a,4,11a-tetrahydro-1H-pyrrolo[3',4':4,5]-pyrido[1,2-a]indole-1,12(2H)-dione of melting point 228°–229° C.

(iv) Raney nickel was added to a suspension of 12 g of the product of (iii) in 600 ml of ethanol and 300 ml of water. The mixture was heated to reflux for 3.25 hours, cooled and decanted. The ethanol was removed under reduced pressure and the residue was extracted with ethyl acetate. The catalyst was washed with 300 ml of ethyl acetate and the organic phase was washed with water, dried and concentrated. The precipitate formed was filtered off to give 5.4 g of 2-benzyl-2,3,3a,4,11,11a-hexahydro-1H-pyrrolo[3',4':4,5]pyrido-[1,2-a]indol-1one of melting point 121°–123° C.

(v) A solution of 10 g of the product of (iv) in 150 ml of THF was added to a stirred 1M solution of borane in 60 ml of THF at 0° C. under nitrogen. The resulting solution was heated to reflux for 1.5 hours, cooled, treated with 30 ml of methanol and 15 ml of 5M sodium hydroxide solution and subsequently heated to reflux for 1.5 hours. The solvent was removed under reduced pressure and the residue was partitioned between dichloromethane and water. The organic phase was washed with saturated sodium bicarbonate solution and with water, dried and evaporated to dryness to give 8 g of cis-2-benzyl-2,3,3a,4,11,11a-hexahydro-1H-pyrrolo[3',4':4,5]pyrido[1,2-a]indole of melting point 91°–93° C.

(vi) A solution of 23.5 g of the product of (v) in 500 ml of methanol was added to 12 g of 10% palladium-on-charcoal and 24 g of ammonium formate. The mixture was heated to reflux under a nitrogen atmosphere for 2.5 hours. The cooled mixture was filtered and the filter residue was washed with methanol. The filtrate and washings were evaporated and the residue was partitioned between dichloromethane and water. The aqueous phase was extracted with dichloromethane and the organic extracts were dried and evaporated to give 16.9 g of cis-2,3,3a,4,11,11a-hexahydro-1H-pyrrolo[3',4':4,5]-pyrido[1,2-a]indole.

(vii) A stirred solution of the product of (vi) in 500 ml of dichloromethane was treated at 0° C. under a nitrogen atmosphere with 18.6 g of di-tert.butyl dicarbonate and 8.7 g of triethylamine. The solution obtained was stirred for 18 hours, washed with water, dried and the solvent was evaporated. The residue was crystallized from diethyl ether/dichloromethane to give 15.2 g of cis-2-(tert.butoxycarbonyl)-2,3,3a,4,11,11a-hexahydro-1H-pyrrolo[3',4':4,5]-pyrido[1,2-a]indole of melting point 143°–144° C.

(viii) 1.95 g of oxalyl chloride were added to a solution of 4.9 g of the product of (vii) in 150 ml of dichloromethane at 0° C. under a nitrogen atmosphere. After 15 minutes, the solvent was removed under reduced pressure and the residue was dissolved in 150 ml of dichloromethane. 2.97 g of 1-methyl-3-indolylacetic acid and 6.5 ml of triethylamine were added to this solution at 0° C. The mixture was then stirred for 72 hours. The solvent was removed by evaporation and the residue was purified by chromatography on silica gel using ethyl acetate/n-hexane (1:1) for the elution to give 2.1 g of cis-3-[2-tert.butoxycarbonyl)-2,3,3a,4, 11,11a-hexahydro-1H-pyrrolo[3',4':4,5]pyrido[1,2-a]indol-10-yl]-4-(1-methyl-3-indolyl)furan-2,5-dione of melting point 209° C. after recrystallization from ethyl acetate/n-hexane.

EXAMPLE 6

A solution of 120 mg of cis-[3-2,3,3a,4,11,11a-hexahydro-2-methyl-1H-pyrrolo[3',4':4,5]pyrido[1,2-a]indol-10-yl]-4-(1-methyl-3-indolyl)furan-2,5-dione acetate in 6 ml of DMF and 5 ml of 33% aqueous ammonia was heated to 120° C. in a sealed vessel for 3 hours. The solvent was removed under reduced pressure and the residue was partitioned between ethyl acetate and aqueous sodium bicarbonate solution. The organic phase was dried, concentrated and treated with a saturated solution of hydrogen chloride in ethyl acetate. The obtained precipitate was filtered off and dried to give 80 mg of cis-3-[2,3,3a,4,11,11a-hexahydro-2-methyl-1H-pyrrolo[3',4':4,5]pyrido-[1,2-a]indol-10-yl]-4-(1-methyl-3-indolyl)-1H-pyrrole-2,5-dione hydrochloride of melting point 308°-310° C.

The furandione acetate used as the starting material was prepared as follows:

(i) A stirred solution of 5 g of cis-3-[2-(tertbutoxycarbonyl)-2,3,3a,4,11,11a-hexahydro-1H-pyrrolo[3',4':4,5]-pyrido[1,2-a]indol-10-yl]-4-(1-methyl-3-indolyl)furan-2,5-dione [prepared as described in Example 5(viii)] in 200 ml of dichloromethane was treated with 30 ml of trifluoroacetic acid. After 0.5 hour the solvent was removed under reduced pressure and the residue was purified by chromatography on silica gel using dichloromethane/methanol/acetic acid/water (90:18:3:2) for the elution. Removal of the solvent gave 4.5 g of cis-3-[2,3,3a,4,11, 11a-hexahydro-1H-pyrrolo[3',4':4,5-]pyrido[1,2-a]indol-10-yl]-4-(1-methyl-3-indolyl)furan-2,5-dione trifluoroacetate of melting point 199°-201° C.

(ii) 28.5 mg of sodium cyanoborohydride were added to a stirred solution of 250 mg of the product of (i) and 67.5 mg of 40% aqueous formaldehyde in 33 ml of acetonitrile. After 0.5 hour the solvent was removed by evaporation and the residue was purified by chromatography on silica gel using dichloromethane/methanol/acetic acid/water (90:18:3:2) for the elution. Evaporation gave 140 mg of cis-3-[2,3,3a,4,11,11a-hexahydro-2-methyl-1H-pyrrolo[3',4':4,5]pyrido[1,2-a]indol-10-yl]-4-(1-methyl-3-indolyl)furan-2,5-dione acetate. A sample of this solid was stirred with a saturated solution of hydrogen chloride in ethyl acetate and the resulting precipitate was filtered off and dried to give cis-3-[2,3,3a,4,11,11a-hexahydro-2-methyl-1H-pyrrolo[3',4':4,5]pyrido[1,2-a]indol-10-yl]-4-(1-methyl-3-indolyl)furan-2,5-dione hydrochloride of melting point 183°-186° C.

EXAMPLE 7

A solution of 200 mg of cis-3-[2,3,3a,4,11,11a-hexahydro-1H-pyrrolo[3',4':4,5]pyrido[1,2-a]indol-10-yl]-4-(1-methyl-3-indolyl)furan-2,5-dione trifluoroacetate [prepared as described in Example 6(i)] and 760 mg of benzaldehyde in 30 ml of methanol was shaken with 20 mg of 10% palladium-on-charcoal under a hydrogen atmosphere. The catalyst was filtered off and the filtrate was evaporated to dryness. The residue was purified by chromatography on silica gel using methanol/dichloromethane (1:19) for the elution to give an oil which was dissolved in 4 ml of DMF. The solution obtained was treated with 2.5 g of 1,1,1,3,3,3-hexamethyldisilazane and then 250 mg of methanol and the mixture was stirred at room temperature for 4 days. The solvent was removed by evaporation and the residue was partitioned between ethyl acetate and sodium bicarbonate solution. The organic phase was dried, concentrated and then treated with a saturated solution of hydrogen chloride in ethyl acetate to give a precipitate which was filtered off and dried. There were thus obtained 60 mg of cis-3-[2-benzyl-2,3,3a,4,11,11a-hexahydro-1H-pyrrolo[3',4':4,5]pyrido[1,2-a]indol-10-yl]-4-(1-methyl-3-indolyl)-1H-pyrrole-2,5-dione hydrochloride of melting point 228°-232° C.

EXAMPLE 8

A stirred suspension of 200 mg of cis-3-[2,3,3a,4,11,11a-hexahydro-1H-pyrrolo[3',4':4,5]pyrido[1,2-a]-indol-10-yl]-4-(1-methyl-3indolyl)furan-2,5-dione trifluoroacetate [prepared as described in Example 6(i)] in 15 ml of acetic acid was treated with 100 mg of acetone. After 5 minutes, 38 mg of sodium borohydride were added. The mixture was then heated to 50° C. for 10 minutes. A further 200 mg of acetone and 50 mg of sodium borohydride were added and the mixture was heated at 50° C. for 1.5 hours. The solvent was removed under reduced pressure and the residue was purified by chromatography on silica gel using methanol/dichloromethane (1:9) for the elution. The obtained oil was dissolved in 5 ml of DMF and the solution obtained was treated with 2.5 g of 1,1,1,3,3,3-hexamethyldisilazane followed by 250 mg of methanol and stirred at room temperature for 18 hours. The solvents were removed by evaporation and the residue was partitioned between ethyl acetate and aqueous sodium bicarbonate solution. The organic extracts were dried and concentrated. 0.5 ml of a saturated solution of hydrogen chloride in ethyl acetate was then added to give a precipitate which was filtered off and dried. There were thus obtained 80 mg of cis-3-[2-isopropyl-2,3,3a,4,11,11a-hexahydro-1H-pyrrolo[3',4':4,5]pyrido[1,2-a]indol-10-yl]-4-(1-methyl-3-indolyl)-1H-pyrrole-2,5-dione hydrochloride of melting point 318°-320° C.

EXAMPLE 9

A stirred solution of 200 mg of cis-3-[2,3,3a, 4,11,11a-hexahydro-1H-pyrrolo[3',4':4,5]pyrido[1,2-a]indol-10-yl]-4-(1-methyl-3-indolyl)furan-2,5-dione trifluoroacetate [prepared as described in Example 6(i)] in 40 ml of acetic acid was heated to 55° C. 67 mg of sodium borohydride were then added and the solution obtained was heated at 55° C. for 1 hour. The solvent was removed under reduced pressure and the residue was purified by chromatography on silica gel using methanol/dichloromethane (1:9) for the elution. The obtained oil was dissolved in 2 ml of DMF and the solution obtained was treated with 1 g of 1,1,1,3,3,3-hexamethyldisilazane followed by 100 mg of methanol. The mixture was stirred for 18 hours, the solvents were removed under reduced pressure and the residue was partitioned between ethyl acetate and aqueous sodium bicarbonate solution. The organic extracts were dried, concentrated and treated with a saturated solution of hydrogen chloride in ethyl acetate. The obtained precipitate was filtered off and dried to give 35 mg of cis-3-[2-ethyl-2,3,3a,4,11,11a-hexahydro-1H-pyrrolo[3',4':4,5-]pyrido[1,2-a]indol-10-yl]-4-(1-methyl-3-indolyl)-1H-pyrrole-2,5-dione hydrochloride of melting point 327°-329° C.

EXAMPLE 10

A solution of 4.5 g of cis-3-[2,3,3a,4,11,11a-hexahydro-1H-pyrrolo[3',4':4,5]pyrido[1,2-a]indol-10-yl]-4-(1-methyl-3-indolyl)furan-2,5-dione trifluoroacetate [prepared as described in Example 6(i)] and 6 g of 40% aqueous formaldehyde in 200 ml of methanol was heated to reflux for 2.5 hours with Raney nickel. The cooled solution was filtered and the filtrate was evaporated. The obtained solid was dissolved in 20 ml of DMF and 20 ml of 33% aqueous ammonia and the solution obtained was heated at 140° C. in a sealed vessel. The cooled solution was partitioned between ethyl acetate and sodium bicarbonate solution. The organic extracts were dried and evaporated. The residue was purified by chromatography on silica gel using dichloromethane/methanol/acetic acid/water (90:18:3:2) for the elution. Crystallization from methanol gave 70 mg of cis-3-[2-formyl-2,3,3a,4,11,11a-hexahydro-1H-pyrrolo[3′,4′:4,5]pyrido[1,2-a]indol-10-yl]-4-(1-methyl-3-indolyl)-1H-pyrrole-2,5-dione of melting point 334°–336° C.

EXAMPLE 11

(A) A mixture of 0.59 ml of 1,1,1,3,3,3-hexamethyldisilazane and 45 mg of methanol was added to a solution of 150 mg of 3-[1-(tert.butoxy-carbonyl)-1′,3′-dihydrospiro[pyrrolidine-3,2′-pyrrolo[1,2-a]indol]-9′-yl]-4-(1-methyl-3-indolyl)-furan-2,5-dione in 10 ml of DMF and stirred for 72 hours. The solvent was removed by evaporation and the residue was treated with 10 ml of methanol. After evaporation, the residue was subjected to chromatography on silica gel using dichloromethane/ethyl acetate (4:1) for the elution. There were obtained 120 mg of 3-[1-(tert.butoxycarbonyl)-1′,3′-dihydrospiro[pyrrolidine-3,2′-pyrrolo[1,2-a]indol]-9′-yl]-4-(1-methyl-3-indolyl)-1H-pyrrole-2,5-dione of melting point 232°–235° C.

(B) A suspension of 110 mg of the product of (A) in 1 ml of ethyl acetate was treated with 5 ml of a saturated solution of hydrogen chloride in ethyl acetate and stirred for 24 hours. The suspension was filtered and the solid was dried to give 85 mg of 3-[1′,3′-dihydrospiro[pyrrolidine-3,2′-pyrrolo[1,2-a]indol]-9′-yl]-4-(1-methyl)-3-indolyl)-1H-pyrole-2,5-dione hydrochloride of melting point 342° C. (decomposition).

The furandione starting material was prepared as follows:

(i) A solution of 17.7 g of ethyl 2-(ethoxy-carbonyl)-2,3-dihydro-1-oxo-1H-pyrrolo[1,2-a]indole-2-acetate in 200 ml of methanol was treated under a nitrogen atmosphere with 1.5 g of 10% palladium-on-charcoal and 10 g of ammonium formate. The mixture was heated at reflux for 1.5 hours, then cooled and filtered. The filtrate was concentrated and the residue was partitioned between ethyl acetate and water. The organic layer was washed with sodium chloride solution and dried. Evaporation of the solvent gave 16.5 g of ethyl 2-(ethoxycarbonyl)-2,3-dihydro-1-hydroxy-1H-pyrrolo[1,2-a]indole-2-acetate.

(ii) A solution of 16.5 g of the product of (i) in 200 ml of dichloromethane was treated under a nitrogen atmosphere with 14 ml of triethylamine and 7.6 g of acetic anhydride. Then the solvent was removed by evaporation. The residue was evaporated with toluene and then dissolved in methanol under a nitrogen atmosphere. 1.5 g of 10% palladium-on-charcoal and 10 g of ammonium formate were added and the mixture was heated at reflux for 4 hours. The suspension was cooled and filtered, and the filtrate was concentrated. The residue was partitioned between ethyl acetate and water. The organic phase was dried and concentrated. Chromatography of the residue on silica gel using ethyl acetate/n-hexane (1:3) for the elution gave 9.65 g of ethyl 2-(ethoxycarbonyl)-2,3-dihydro-1H-pyrrolo[1,2-a]indole-2-acetate.

(iii) A solution of 1.2 g of the product of (ii) in 25 ml of ethanol was treated with 7.6 ml of 2M aqueous sodium hydroxide and the mixture was heated under reflux for 17 hours. The solution was concentrated and the residue was diluted with water. The solution was washed with ethyl acetate and acidified with 2M aqueous hydrochloric acid. The mixture was extracted with dichloromethane and the extracts were washed with sodium chloride solution. The organic phase was dried and concentrated. Trituration of the residue with diethyl ether gave 714 mg of 2-carboxy-2,3-dihydro-1H-pyrrolo[1,2-a]indole-2-acetic acid of melting point 211°–215° C. (decomposition).

(iv) A mixture of 650 mg of the product of (iii) and 480 mg of ammonium carbonate was heated at 200° C. under a nitrogen atmosphere. After cooling, the residue was partitioned between dichloromethane and water. The organic phase was dried and concentrated to give 594 mg of 1′,3′-dihydrospiro[pyrrolidine-3,2′-pyrrolo[1,2-a]indole]-2,5-dione of melting point 215°–220° C.

(v) A solution of 580 mg of the product of (iv) in 5 ml of THF was added under a nitrogen atmosphere to a stirred suspension of 920 mg of lithium aluminum hydride in 10 ml of THF. The mixture was heated at reflux for 2 hours, cooled and treated with 10 ml of water and 2 ml of 2M aqueous sodium hydroxide. The suspension was filtered and the solid was washed with ethyl acetate. The filtrate was separated and the aqueous layer was extracted with ethyl acetate. The organic solutions were washed with sodium chloride solution and concentrated to give 510 mg of 1′,3′-dihydrospiro[pyrrolidine-3,2′-pyrrolo[1,2-a]indole] of melting point 90°–92° C.

(vi) A solution of 500 mg of the product of (v) in 15 ml of dichloromethane was treated with 0.4 ml of triethylamine and 580 mg of di-tert.butyl dicarbonate and stirred for 17 hours. The solvent was removed by evaporation. Chromatography of the residue on silica gel using ethyl acetate/n-hexane (1:2) for the elution gave 440 mg of 1-(tert.butoxycarbonyl)-1′,3′-dihydrospiro[pyrrolidine-3,2′-pyrrolo[1,2-a]indole] of melting point 104°–106° C.

(vii) In a manner analogous to that described in Example 1(vii) from 430 mg of the product of (vi) there were obtained 160 mg of 3-[1-(tert.butoxycarbonyl)-1′,3′-dihydrospiro-[pyrrolidine-3,2′-pyrrolo[1,2-a]indol]-9′-yl]-4-(1-methyl-3-indolyl)-furan-2,5-dione.

EXAMPLE 12

A solution of 360 mg of 3-[1′,3′-dihydro-1-methyl-spiro[pyrrolidine-3,2′-pyrrolo[1,2-a]indol-9′-yl]-4-(1-methyl-3-indolyl)-furan-2,5-dione in 10 ml of DMF was treated with 1.7 ml of 1,1,1,3,3,3-hexamethyldisilazane and 128 mg of methanol. The solution was heated at 60° C. for 17 hours and the solvent was removed by evaporation. The residue was evaporated with 10 ml of methanol and purified by chromatography on silica gel using dichloromethane/methanol (9:1) for the elution. The solid obtained was suspended in ethyl acetate and treated with a saturated solution of hydrogen chloride in ethyl acetate. After stirring, the suspension was filtered and the solid was washed with diethyl ether to give 250 mg of 3-[1′,3′-dihydro-1-methylspiro[pyrrolidine-3,2′-pyrrolo[1,2-a]indol]-9′-yl]-4-(1-methyl-3- indolyl)-1H-pyrrole-2,5-dione hydrochloride of melting point 250°–252° C.

The furandione starting material was prepared as follows:

(i) A solution of 1.96 g of 1',3'-dihydrospiro[pyrrolidine-3,2'-pyrrolo[1,2-a]indole]-2,5-dione [prepared as described in Example 11(iv)] in 10 ml of DMF was added dropwise to a stirred suspension of 330 mg of a 60% dispersion of sodium hydride in mineral oil in 10 ml of DMF. The mixture was treated with 1 ml of iodomethane and stirred for 17 hours. The mixture was diluted with water, neutralized with 1M aqueous hydrochloric acid and extracted with ethyl acetate. The extracts were washed with sodium chloride solution, dried and the solvent was removed by evaporation. Crystallization of the residue from ethyl acetate/n-hexane gave 1.81 g of 1',3'-dihydro-1-methylspiro-[pyrrolidine-3,2'-pyrrolo[1,2-a]indole]-2,5-dione of melting point 154°–156° C.

(ii) In a manner analogous to Example 11(v), from 1.8 g of the product of (i) there were obtained 1.07 g of 1',3'-dihydro-1-methylspiro-[pyrrolidine-3,2'-pyrrolo[1,2-a]indole] of melting point 81°–83° C.

(iii) A solution of 1.03 g of the product of (ii) in 10 ml of ethyl acetate was treated with 2 ml of a saturated solution of hydrogen chloride in ethyl acetate. After 1 hour, the solvent was removed by evaporation and the residue was dissolved in 20 ml of dichloromethane under a nitrogen atmosphere. The solution was cooled to −78° C. and treated with 0.4 ml oxalyl chloride. After 15 minutes, a mixture of 860 mg of 1-methylindole-3-acetic acid and 2.5 ml of triethylamine dissolved in 20 ml of dichloromethane was added. The mixture was stirred at −78° C. for 1 hour and then left to warm to room temperature. The solvent was removed by evaporation and the residue was subjected to chromatography on silica gel using dichloromethane/methanol/acetic acid/water (120:14:3:2) for the elution. The product was dissolved in dichloromethane and the solution was washed with saturated aqueous sodium bicarbonate. The organic phase was dried and evaporated to give 380 mg of 3-[1',3'-dihydro-1-methylspiro[pyrrolidine-3,2'-pyrrolo[1,2-a]indole-9'-yl]-4-(1-methyl-3-indolyl)-furan-2,5-dione.

EXAMPLE 13

In a manner analogous to that described in Example 11, from 285 mg of 3-[8,9-dihydro-1'-methylspiro[pyrido[1,2-a]indole-7(6H),3'-pyrrolidin]-10-yl]-4-(1-methyl-3-indolyl)-furan-2,5-dione there were obtained 232 mg of 3-[8,9-dihydro-1'-methylspiro[pyrido[1,2-a]indole-7(6H),3'-pyrrolidin]-10-yl]-4-(1-methyl-3-indolyl)-1H-pyrrole-2,5-dione hydrochloride of melting point 220° C. (decomposition).

The furandione starting material was prepared as follows:

(i) A stirred solution of 2.52 ml of diisopropylamine in 20 ml of THF was cooled in a bath at −78° C. under an argon atmosphere and treated with 11.25 ml of a 1.6M solution of n-butyllithium in n-hexane. The mixture was treated with a solution of 2.85 g of ethyl 6,7,8,9-tetrahydropyrido[1,2-a]indole-7-carboxylate in 80 ml of THF. After 10 minutes, 1.46 ml of ethyl bromoacetate were added and the cooling bath was removed. The mixture was stirred and then diluted with diethyl ether. The solution was washed in succession with saturated aqueous ammonium chloride, water and sodium chloride solution and then dried. The solvent was removed by evaporation and the residue was subjected to chromatography on silica gel using ethyl acetate/n-hexane (1:9) for the elution to give 2.55 g of ethyl 7-(ethoxycarbonyl)-6,7,8,9-tetrahydropyrido-[1,2-a]indole-7-acetate.

(ii) In a manner analogous to that described in Example 11(iii), from 2.5 g of the product of (i) there were obtained 1.95 g of 7-(carboxy)-6,7,8,9-tetrahydropyrido[1,2-a]indole-7-acetic acid of melting point 185°–188° C.

(iii) In a manner analogous to that described in Example 11(iv), from 2.02 g of the product of (ii) there were obtained 1.8 g of 8,9-dihydrospiro[pyrido[1,2-a]indole-7(6H),3'-pyrrolidine]-2',5'-dione of melting point 208°–210° C.

(iv) In a manner analogous to that described in Example 12(i), from 1.04 g of the product of (iii) there were obtained 780 mg of 8,9-dihydro-1'-methylspiro[pyrido[1,2-a]indole-7(6H),3'-pyrrolidine]-2',5'-dione of melting point 158°–164° C.

(v) In a manner analogous to that described in Example 11(v), from 930 mg of the product of (iv) there were obtained 470 mg of 8,9-dihydro-1'-methylspiro[pyrido[1,2-a]indole-7(6H),3'-pyrrolidine] of melting point 55°–58° C.

(vi) In a manner analogous to that described in Example 12(iii), from 460 mg of the product of (v) there were obtained 280 mg of 3-[8,9-dihydro-1'-methylspiro[pyrido[1,2-a]indole-7(6H),3'-pyrrolidin]-10-yl]-4-(1-methyl-3-indolyl)-furan-2,5-dione of melting point 238°–240° C.

EXAMPLE 14

A mixture of 1.21 g of 1,1,1,3,3,3-hexamethyldisilazane and 132 mg of methanol was added to a solution of 400 mg of trans-3-(2,3,3a,4,11,11a-hexahydro-2-methyl-1H-pyrrolo[3',4':4,5]-pyrido[1,2-a]indol-10-yl)-4-(1-methyl-3-indolyl)furan-2,5-dione hydrochloride in 30 ml of DMF and stirred for 48 hours. A further 100 mg of methanol and 0.95 g of 1,1,1,3,3,3-hexamethyldisilazane were added, the mixture was heated to 45° C. for 2 hours and then left to stand at room temperature. The solvent was removed under reduced pressure and the residue was dissolved in ethyl acetate, dichloromethane and methanol. The solution obtained was washed with saturated sodium bicarbonate solution and the organic layer was concentrated. A saturated solution of hydrogen chloride in ethyl acetate was added and the precipitate obtained was filtered off. The solid was suspended in water and stirred, then filtered off and dried. The solid obtained was suspended in ethyl acetate and stirred, then filtered off and dried to give 235 mg of trans-3-(2,3,3a,4,11,11a-hexahydro-2-methyl-1H-pyrrolo[3',4':4,5]pyrido[1,2-a]indol-10-yl)-4-(1-methyl-3-indolyl)-1H-pyrrole-2,5-dione hydrochloride of melting point >330° C.

The furandione hydrochloride used as the starting material was prepared as follows:

(i) From a mixture of 29.3 g of diethyl 6,7-dihydro-9-hydroxypyrido[1,2-a]indole-7,8-dicarboxylate, 100 ml of pyridine and 30 ml of acetic anhydride, the solvents were removed under reduced pressure and the residue was partitioned between ethyl acetate and 2M hydrochloric acid. The organic extract was washed with saturated sodium bicarbonate solution and water, dried and evaporated to give 33 g of diethyl 9-acetoxy-6,7-dihydropyrido[1,2-a]indole-7,8-dicarboxylate.

(ii) A solution of 33 g of the product of (i) in 250 ml of ethanol and 25 g of triethylamine was hydrogenated over 10% palladium-on-charcoal. The catalyst was filtered off and the filtrate was evaporated. The residue was partitioned between ether and water and the organic layer was washed in succession with 2M hydrochloric acid, water and saturated sodium bicarbonate solution. The organic extract was dried and evaporated. The oil obtained was dissolved in ethanol and the solution was treated with sodium ethoxide and stirred for 1 hour. The solution was cooled to 0° C. and the solid was filtered off and dried to give 15.9 g of trans-diethyl 6,7,8,9-tetrahydropyrido[1,2-a]indole-7,8-dicarboxylate of melting point 74°-76° C.

(iii) A stirred solution of 10.0 g of the product of (ii) in 150 ml of THF was treated at 0° C. under a nitrogen atmosphere with 40 ml of a 1M solution of lithium aluminium hydride in diethyl ether. After stirring, 1.4 ml of water were added, followed by 2.3 ml of 2M sodium hydroxide and 3.5 ml of water. The precipitate was filtered off and washed with THF/diethyl ether (1:1). The filtrate was evaporated to give 6.8 g of trans-6,7,8,9-tetrahydropyrido[1,2-a]indole-7,8-dimethanol of melting point 162°-163° C.

(iv) A stirred solution of 6.8 g of the product of (iii) in 150 ml of dichloromethane was treated with 35 ml of triethylamine and then 11.3 g of methanesulphonic anhydride were added. The solution was stirred under a nitrogen atmosphere and then diluted with dichloromethane. The solution was washed with water, 2M hydrochloric acid and water, dried and evaporated. Ethanol was added and the solvent was removed under reduced pressure to give 10.3 g of trans-6,7,8,9-tetrahydro-7,8-bis[(methanesulphonyloxy)methyl]pyrido[1,2-a]indole. A sample was purified by chromatography on silica gel using ethyl acetate/petroleum ether (2:1) for the elution to give a solid of melting point 139°-141° C.

(v) A solution of 8.0 g of the product of (iv) and 20.0 g of benzylamine in 700 ml of toluene was heated to reflux under a nitrogen atmosphere. The solvent was removed under reduced pressure and the residue was purified by chromatography on silica gel using methanol/dichloromethane (1:50 to 1:20) for the elution to give 6.55 g of trans-2-benzyl-2,3,3a,4,11,11a-hexahydro-1H-pyrrolo[3',4':4,5]pyrido[1,2-a]indole of melting point 114°-116° C.

(vi) A solution of 3.0 g of the product of (v) in 150 ml of methanol was treated with 3.0 g of ammonium formate and 1.2 g of 10% palladium-on-charcoal. The mixture was heated to reflux and then filtered. The catalyst was washed with methanol and the filtrates were evaporated. The residue was partitioned between ethyl acetate and water and the solid was filtered off. This solid was suspended in a saturated solution of hydrogen chloride in ethyl acetate and stirred, then filtered off and dried to give 2.0 g of trans-2,3,3a,4,11,11a-hexahydro-1H-pyrrolo[3',4':4,5]-pyrido[1,2-a]indole hydrochloride of melting point 308°-311° C.

(vii) A solution of 1.97 g of the product of (vi) in 300 ml of dichloromethane was treated with 1.72 g of triethylamine. The mixture obtained was cooled to 0° C. under a nitrogen atmosphere and was treated with 1.87 g of di-tert.butyl dicarbonate. After stirring, the mixture was washed with water, 2M hydrochloric acid, water and saturated sodium bicarbonate solution and then dried. The solvent was removed under reduced pressure to give 2.4 g of a solid. A sample was triturated with petroleum ether to give trans-2-(tert.-butoxycarbonyl)-2,3,3a,4,11,11a-hexahydro-1H-pyrrolo[3',4':4,5]-pyrido[1,2-a]indole of melting point 217°-218° C.

(viii) 1.08 g of oxalyl chloride were added to a solution of 2.7 g of the product of (vii) in 100 ml of dichloromethane at 0° C. After 0.25 hour, the solvent was removed under reduced pressure and the residue was dissolved in dichloromethane. The solution was added to a stirred solution of 2.5 ml triethylamine and 1.64 g of 1-methylindole-3-acetic acid in 50 ml of dichloromethane. After 24 hours, the solution was washed with water and saturated sodium bicarbonate solution, dried and evaporated. The residue was purified by chromatography on silica gel using ethyl acetate/petroleum ether (1:1) for the elution to give 1.2 g of trans-3-[2-(tert.butoxycarbonyl)-2,3,3a,4,11,11a-hexahydro-1H-pyrrolo[3',4':4,5]pyrido[1,2-a]indol-10-yl]-4-(1-methyl-3-indolyl)furan-2,5-dione of melting point 265°-266° C.

(ix) A suspension of 900 mg of the product of (viii) in 5 ml of ethyl acetate was treated with 10 ml of a saturated solution of hydrogen chloride in ethyl acetate. After 2 hours, the solid was filtered off and dried to give 720 mg of trans-3-[2,3,3a,4,11,11a-hexahydro-1H-pyrrolo[3',4':4,5]pyrido[1,2-a]indol-10-yl]-4-(1-methyl-3-indolyl)furan-2,5-dione hydrochloride of melting point >340° C.

(x) A suspension of 640 mg of the product of (ix) in 190 ml of methanol was treated with Raney nickel and 325 mg of 40% aqueous formaldehyde and the mixture obtained was heated to reflux for 3 hours. After each 0.5 hour a further 250 mg of aqueous formaldehyde were added. The cooled supernatant was decanted off and the residue was washed with methanol. The organic solution was evaporated and the residue was suspended in ethyl acetate and treated with a saturated solution of hydrogen chloride in ethyl acetate. The solid was filtered off and dried to give 445 mg of trans-3-[2,3,3a,4,11,11a-hexahydro-2-methyl-1H-pyrrolo[3',4':4,5]pyrido[1,2-a]indol-10-yl]-4-(1-methyl-3-indolyl)furan-2,5-dione hydrochloride of melting point 244°-247° C.

EXAMPLE 15

In a manner analogous to that described in Example 11, from trans-3-[2-(tert.butoxycarbonyl)-2,3,3a,4,11,-11a-hexahydro-1H-pyrrolo[3',4':4,5]pyrido[1,2-a]indol-10-yl]-4-(1-methyl-3-indolyl)furan-2,5-dione [prepared as described in Example 14], there was obtained trans-3-[2,3,3a,4,11,11a-hexahydro-1H-pyrrolo[3',4':4,5-]pyrido[1,2-a]indol-10-yl]-4-(1-methyl-3-indolyl)-1H-pyrrole-2,5-dione hydrochloride of melting point 269°-273° C.

EXAMPLE 16

In a manner analogous to that described in Example 14, from (+)-trans-2,3,3a,4,11,11a-hexahydro-1H-pyrrolo[3',4':4,5]pyrido[1,2-a]indole formate there was obtained (+)-trans-3-[2,3,3a,4,11,11a-hexahydro-2-methyl-1H-pyrrolo[3',4':4,5]-pyrido[1,2-a]indol-10-yl]-4-(1-methyl-3-indolyl)-1H-pyrrole-2,5-dione hydrochloride of melting point 325°-328° C.; $[\alpha]_D^{20} = +65.1°$ (MeOH, c=0.06).

The pyridoindole formate used as the starting material was prepared as follows:

(i) A suspension of 11.0 g of trans-6,7,8,9-tetrahydro-7,8-bis[(methanesulphonyloxy)methyl]pyrido[1,2-a]indole [prepared as described in Example 14(iv)] in 60 ml of ethanol was treated with 26 ml of (S)-α-methylbenzylamine and heated to reflux for 18 hours. The cooled solution was concentrated and the precipitate was filtered off and purified by chromatography on silica gel using ethyl acetate/petroleum ether (2:1) for the elution. There were obtained 2.1 g of trans-2,3,3a,4,11,11a-hexahydro-2-[alpha(S)-methylbenzyl]-1H-pyrrolo[3',4':4,5]pyrido[1,2-a]indole, diastereomer A, of melting point 153° C., $[\alpha]_D^{20} = +17.7°$ (CHCl$_3$, c=0.51), and 1.6 g of trans-2,3,3a,4,11,11a-hexahydro-2-[alpha(S)-methylbenzyl]-1H-pyrrolo[3',4':4,5-]pyrido[1,2-a]indole, diastereomer B, of melting point 154°-156° C.; $[\alpha]_D^{20} = -54.2°$ (CHCl$_3$, c=0.49).

(ii) A suspension of 1.4 g of the obtained diastereomer A in 80 ml of methanol was treated with 10% palladium-on-charcoal and 1.4 g of ammonium formate. The mixture was heated to reflux, then cooled and filtered. The catalyst was washed with methanol and the filtrates were evaporated. Crystallization from ethyl acetate gave 0.87 g of (+)-trans-2,3,3a,4,11,11a-hexahydro-1H-pyrrolo[3',4':4,5]pyrido[1,2-a]indole formate of melting point 188°-190° C.; $[\alpha]_D^{20} = +49°$ (MeOH, c=0.04).

EXAMPLE 17

In a manner analogous to that described in Example 14, from (−)-trans-2,3,3a,4,11,11a-hexahydro-1H-pyrrolo[3',4':4,5]-pyrido[1,2-a]indole formate there was obtained (−)-trans-3-[2,3,3a,4,11,11a-hexahydro-2-methyl-1H-pyrrolo[3',4':4,5]-pyrido[1,2-a]indol-10yl]-4-(1-methyl-3-indoly)-1H-pyrrole-2,5-dione hydrochloride of melting point 339°-340° C.; $[\alpha]_D^{20} = -108°$ (MeOH, c=0.02).

The pyridoindole formate used as the starting material was prepared as follows:

In a manner analogous to that described in Example 16 (ii), from trans-2,3,3a,4,11,11a-hexahydro-2-[alpha(S)-methylbenzyl]-1H-pyrrolo[3',4,4,5]pyrido[1,2-a]indole, diastereomer B, [prepared as described in Example 16(i)] there was obtained (−)-trans-2,3,3a,4,11,-11a-hexahydro-1H-pyrrolo[3',4':4,5]pyrido[1,2-a]indole formate of melting point 208°-212° C.; $[\alpha]_D^{20} = -49.9°$ (MeOH, c=0.05).

EXAMPLE 18

In a manner analogous to that described in Example 15, from (+)-trans-3-[2-(tert.butoxycarbonyl)-2,3,3a,4,11,11a-hexahydro-1H-pyrrolo[3',4':4,5-]pyrido[1,2-a]indol-10-yl]-4-(1-methyl-3-indolyl)furan-2,5-dione, prepared in a manner analogous to that described in Example 14 (vii) and (viii) from (+)-trans-2,3,3a,4,11,11a-hexahydro-1H-pyrrolo[3',4':4,5]-pyrido[1,2-a]indole formate [prepared as described in Example 16]), there was obtained (+)-trans-3-(2,3,3a,4,11,11a-hexahydro-1H-pyrrolo[3',4':4,5-]pyrido[1,2-a]indole-10-yl)-4-(1-methyl-3-indolyl)-1H-pyrrole-2,5-dione hydrochloride of melting point 276°-280° C.; $[\alpha]_D^{20} = +50.1°$ (MeOH, c=0.05).

EXAMPLE 19

In a manner analogous to that described in Example 15, from (−)-trans-2,3,3a,4,11,11a-hexahydro-1H-pyrrolo[3',4':4,5]pyrido[1,2-a]indole formate [prepared as described in Example 17] there was obtained (−)-trans-3-[2,3,3a,4,11,11a-hexahydro-1H-pyrrolo[3',4':4,5-]pyrido[1,2-a]indol-10-yl]-4-(1-methyl-3-indolyl)-1H-pyrrole-2,5-dione hydrochloride of melting point >330° C. (decomposition); $[\alpha]_D^{20} = -59.6°$ (MeOH, c=0.06).

EXAMPLE 20

A solution of 100 mg of (+)-trans-3-[2,3,3a,4,11,11a-hexahydro-1H-pyrrolo[3',4':4,5]pyrido[1,2-a]indol-10-yl]-4-(1-methyl-3-indolyl)furan-2,5-dione hydrochloride in 4 ml of DMF and 4 ml of 33% aqueous ammonia was heated to 140° C. in a sealed vessel. The solvent was removed under reduced pressure and the residue was triturated with ethyl acetate to give 12 mg of (+)-trans-3-[2-formyl-2,3,3a,4,11,11a-hexahydro-1H-pyrrolo[3',4':4,5]pyrido[1,2-a]indol-10-yl]-4-(1-methyl-3-indolyl)-1H-pyrrole-2,5-dione of melting point 316°-318° C.; $[\alpha]_D^{20} = +59°$ (MeOH, c=0.05).

The furandione hydrochloride, melting point >340° C., used as the starting material was prepared as described in Example 14 from (+)-trans-2,3,3a,4,11,11a-hexahydro-1H-pyrrole[3',4':4,5]-pyrido[1,2-a]indole formate (obtained as described in Example 16).

EXAMPLE 21

In a manner analogous to that described in Example 1(A), from 3-[7,9-dihydro-1'-methylspiro[6H-pyrido[1,2-a]indole-8,3'-piperidin]-10-yl]-4-(1-methyl-3-indolyl)furan-2,5-dione acetate there was obtained 3-[7,9-dihydro-1'-methylspiro[6H-pyrido[1,2-a]indole-8,3'-piperidin]-10-yl]-4-(1-methyl-3-indolyl)-1H-pyrrole-2,5-dione of melting point 144°-146° C.

The furandione used as the starting material was prepared as follows:

(i) A solution of 400 mg of 3-[1-(tert.butoxy-carbonyl)-7',9'-dihydrospiro[piperidine-3,8'(6'H)-pyrido[1,2-a]indol]-10'-yl]-4-(1-methyl-3-indolyl)furan-2,5-dione in 10 ml of ethyl acetate was treated with 10 ml of a saturated solution of hydrogen chloride in ethyl acetate and stirred. The solvent was removed under reduced pressure and the residue was triturated with diethyl ether to give 240 mg of 3-[7',9'-dihydrospiro[-piperidine-3,8'(6'H)-pyrido[1,2-a]indol-10'-yl]-4-(1-methyl-3-indolyl)furan-2,5-dione hydrochloride of melting point 162°-165° C.

(ii) A solution of 238 mg of the product of (i) in 20 ml of DMF was treated with 100 mg of potassium carbonate and 100 mg of dimethyl sulphate. The mixture obtained was stirred, then diluted with water and extracted with dichloromethane. The organic extracts were washed with sodium chloride solution, dried and evaporated. Purification by chromatography on silica gel using dichloromethane/methanol/acetic acid/water (90:21:2:3) for the elution gave 75 mg of 3-[7,9-dihydro-1'-methylspiro[6H-pyrido[1,2-a]indole-8,3'-piperidin]-10-yl]-4-(1-methyl-3-indolyl)furan-2,5-dione acetate of melting point 174°-178° C.

EXAMPLE 22

(A) A mixture of 285 mg of 1,1,1,3,3,3-hexamethyldisilazane and 31 mg of methanol was added to a solution of 100 mg of 3-[2-(tert.butoxy-formamido)-7',9'-dihydrospiro[cyclopentane-1,8'(6'H)-pyrido[1,2-a]indol]-10'-yl]-4-(1-methyl-3-indolyl)furan-2,5-dione in 2 ml of DMF and stirred at 60° C. under a nitrogen atmosphere. The mixture was poured into 10 ml of water and extracted with ethyl acetate. The organic extracts were washed with sodium chloride solution, dried and evaporated to give 85 mg of 3-[2[(tert.butoxyformamido-7',9'-dihydrospiro[cyclopentane-1,8'(6'H)-pyrido[1,2-a]indol]-10'-yl]-4-(1-methyl-3indolyl)-1H-pyrrole-2,5-dione of melting point 113°-114° C.

(B) A solution of 85 mg of the product of (A' in 5 ml of ethyl acetate was treated with 10 ml of a saturated solution of hydrogen chloride in ethyl acetate and the mixture was stirred. The solvent was removed under reduced pressure and the residue was purified by chromatography on silica gel using dichloromethane/methanol/acetic acid/water (90:21:2:3) for the elution to give 22 mg of 3-[2-amino-7',9'-dihydrospiro[cyclopentane-1,8'(6'H)-pyrido[1,2-a]indol]-10'-yl]-4-(1-methyl-3-indolyl)-1H-pyrrole-2,5-dione hydrochloride of melting point 190° C. (decomposition).

The furandione starting material was prepared as follows:

(i) A suspension of 1.5 g of sodium hydride in 50 ml of DMF was treated with a solution of 14.35 g of ethyl 6,7-cihydro-9-hydroxypyrido[1,2-a]indole-8-carboxylate in 50 ml of DMF under a nitrogen atmosphere. The mixture was stirred and was then treated with a solution of 13.7 g of tert.butyl 4-bromobutyrate in 50 ml of DMF. The mixture was then heated to 60° C. for 48 hours, cooled, poured into 500 ml of water and extracted with dichloromethane. The organic extracts were washed with sodium chloride solution, dried and evaporated to give 9.5 g of tert.butyl 8-(ethoxycarbonyl)-6,7,8,9-tetrahydro-9-oxopyrido[1,2-a]indole-8-butyrate of melting point 104° C.

(ii) A solution of 9.5 g of the product of (i) in 200 ml of ethanol was treated with a suspension of Raney nickel in water and the mixture was heated at reflux. The cooled mixture was filtered and the residue was washed with ethyl acetate. The filtrate was extracted with ethyl acetate and the organic extracts were dried and evaporated to give 7.80 g of tert.butyl 8-(ethoxycarbonyl)-6,7,8,9-tetrahydropyrido[1,2-a]indole-8-butyrate.

(iii) A solution of 7.78 g of the product of (ii) in 50 ml of THF was added to a solution of 2.83 g of potassium tert.butoxide in THF. The mixture was stirred under a nitrogen atmosphere, then poured into 100 ml of water and extracted with ethyl acetate. The organic extracts were dried and removed by evaporation to give 1.25 g of tert.butyl 7',9'-dihydro-2-oxospiro[cyclopentane-1,8'(6'H)-pyrido[1,2-a]indole]-3-carboxylate of melting point 129°-131° C.

(iv) A solution of 1.20 g of the product of (iii) in 100 ml of dichloromethane was treated with 5 ml of trifluoroacetic acid at −10° C. under a nitrogen atmosphere. The solution was stirred and then toluene was added. The solvents were removed under reduced pressure and the residue was purified by chromatography on silica gel using dichloromethane/ methanol (95:5) for the elution to give 0.70 g of 7',9'-dihydrospiro[cyclopentane-1,8'(6'H)-pyrido[1,2-a]indol]-2-one of melting point 128°-130° C.

(v) A solution of 0.73 g of hydroxylamine hydrochloride and 1.41 g of potassium hydroxide in water was added to a solution of 0.50 g of the product of (iv) in methanol and the solution obtained was heated to reflux. The cooled reaction mixture was neutralized with a saturated solution of ammonium chloride and extracted with diethyl ether. The ethereal extracts were dried and evaporated to give 0.43 g of 7',9'-dihydrospiro[cyclopentane-1,8'(6'H)-pyrido[1,2-a]indol]-2-one oxime of melting point 211° C. (decomposition).

(vi) A solution of 1.0 g of the product of (v) in THF was added to a suspension of 300 mg of lithium aluminium hydride in THF. The mixture was then heated to reflux, then cooled, poured into 100 ml of water and extracted with diethyl ether. The ethereal extracts were washed with 1M hydrochloric acid and the acid washings were made basic with 2M sodium hydroxide and extracted with dichloromethane. The organic extracts were dried and evaporated to give 550 mg of 7',9'-dihydrospiro[cyclopentane-1,8'(6'H)-pyrido[1,2-a]indol]-2-amine.

(vii) A solution of 850 mg of the product of (vi) in 10 ml of dichloromethane was added to an ice-cold solution of 765 mg of di-tert.butyl dicarbonate and 354 mg of triethylamine in dichloromethane. The mixture was stirred, then washed with water and with saturated sodium bicarbonate, dried and evaporated to give 1.20 g of 2-(tert.butoxyformamido)-7',9'-[cyclopentane-1,8'(6'H)-pyrido[1,2-a]indole.

(viii) 493 mg of oxalyl chloride were added to a solution of 1.20 g of the product of (vii) in 50 ml of dichloromethane at −78° C. A solution of 735 mg of 1-methylindole-3-acetic acid and 1.78 g of triethylamine in 50 ml of dichloromethane was added at −78° C. under a nitrogen atmosphere. The mixture was then stirred at room temperature for 18 hours and the solvent was removed under reduced pressure. The residue was purified by chromatography on silica gel using dichloromethane/methanol (95:5) for the elution to give 643 mg of 3-[2-(tert.butoxyformamido)-7',9'-dihydro-spiro[cyclopentane-1,8'(6'H)-pyrido[1,2-a]indol]-10'-yl]-4-(1-methyl-3-indolyl)furan-2,5-dione of melting point 123°-125° C.

EXAMPLE 23

In a manner analogous to that described in Example 14, from trans-3-[2-(tert.butoxyformamido)-8',9'-dihydrospiro[cyclopropane-1,7'(6'H)pyrido[1,2-a]indol]-10-yl]-4-(1-methyl-3-indolyl)furan-2,5-dione (prepared as described in Example 4) there was obtained trans-3-[8',9'-dihydro-2-dimethylaminospiro[cyclopropane1,7'(6'H)pyrido[1,2-a]indol]-10-yl]-4-(1-methyl-3-indolyl)-1H-pyrrole-2,5-dione hydrochloride of melting point 258°-261° C. (decomposition).

The following Examples illustrate typical pharmaceutical preparations containing compounds provided by the present invention:

EXAMPLE A

Tablets containing the following ingredients may be produced in a conventional manner:

| Ingredient | Per tablet |
| --- | --- |
| Compound of formula I | 5.0 mg |
| Lactose | 125.0 mg |
| Maize starch | 75.0 mg |
| Talc | 4.0 mg |
| Magnesium stearate | 1.0 mg |
| Tablet weight | 210.0 mg |

EXAMPLE B

Capsules containing the following ingredients may be produced in a conventional manner:

| Ingredient | Per capsule |
| --- | --- |
| Compound of formula I | 10.0 mg |
| Lactose | 165.0 mg |
| Maize starch | 20.0 mg |
| Talc | 5.0 mg |
| Capsule fill weight | 200.0 mg |

We claim:
1. A compound of the formula

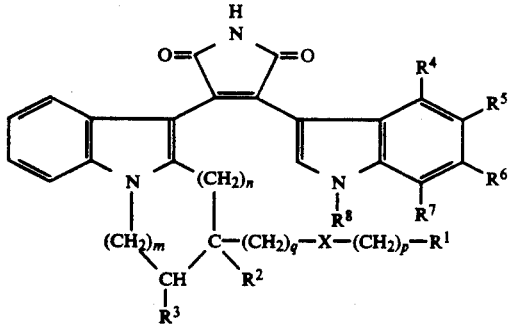

wherein
- $R^1$ and $R^3$ together form a bond and $R^2$ is hydrogen or $R^1$ and $R^2$ together form a bond and $R^3$ is hydrogen;
- $R^4$, $R^5$, $R^6$ and $R^7$ each independently are hydrogen, halogen, $C_{1-7}$ alkyl, halo $C_{1-7}$ alkyl, $C_{1-7}$ alkoxy, nitro, amino, $C_{1-7}$ alkanoylamino, aroylamino, $C_{1-7}$ alkylthio or $C_{1-7}$ alkylsulfonyl;
- $R^8$ is hydrogen, $C_{1-7}$ alkyl or aryl $C_{1-7}$ alkyl;
- X is $-N(R^9)-$ or $-CHN(R^{10},R^{11})-$ in which $R^9$, $R^{10}$ and $R^{11}$ each are hydrogen, $C_{1-7}$ alkyl, aryl $C_{1-7}$ alkyl or $C_{1-7}$ alkanoyl;
- m is 0–2 and n is 1–3, with the proviso that the sum of m and n is 1–3;
- p is 0–4 and q is 0–4, with the proviso that the sum of p and q is 2–4 when X is $-N(R^9)-$, that the sum of p and q is 1–5 when X is $-CHN(R^{10}, R^{11})-$ and $R^1$ and $R^2$ together form a bond, that the sum of p and q is 0–4 when X is $-CHN(R^{10}, R^{11})-$ and $R^1$ and $R^3$ together form a bond, and that p is 1–4 when X is $-N(R^9)-$, $R^1$ and $R^3$ together represent a bond and m is 0, or a pharmaceutically acceptable salt of an acidic compound of formula I with a base or of a basic compound of formula I with an acid.

2. A compound according to claim 1, wherein $R^1$ and $R^3$ together form a bond and $R^2$ is hydrogen, X is $-N(R^9)-$ and m, n, p and q each are 1.

3. A compound according to claim 1, wherein $R^1$ and $R^2$ together form a bond and $R^3$ is hydrogen, X is $-N(R^9)-$, m, n and q are 1 and p is 2.

4. A compound according to any one of claims 2, 3, or 1 wherein $R^4$, $R^5$, $R^6$, and $R^7$ each are hydrogen.

5. A compound according to any one of claims 2, 3, 4 or 1, wherein $R^8$ is alkyl.

6. A compound according to claim 5, wherein $R^8$ is methyl.

7. A compound according to any one of claims 2, 3, 4, 5 or 1, wherein $R^9$ is hydrogen or $C_{1-7}$ alkyl.

8. A compound according to claim 7, wherein $R^9$ is hydrogen or methyl.

9. A compound according to claim 1, wherein $R^{10}$ and $R^{11}$ each are hydrogen or alkyl $C_{1-7}$.

10. A compound according to claim 9, wherein $R^{10}$ and $R^{11}$ each are methyl.

11. A compound according to claim 1 selected from the group consisting of
- 3-[6,7,8,9-Tetrahydrospiro[pyrido[1,2-a]indole-8,3′-pyrrolidin]-10-yl]-4-(1-methyl-3-indolyl)-1H-pyrrole-2,5-dione,
- cis-3-[2,3,3a,4,11,11a-Hexahydro-2-methyl-1H-pyrrolo[3′,4′:4,5]pyrido[1,2-a]indol-10-yl]-4-(1-methyl-3-indolyl)-1H-pyrrole-2,5-dione,
- trans-3-[2,3,3a,4,11,11a-Hexahydro-2-methyl-1H-pyrrolo[3′,4′:4,5]pyrido[1,2-a]indol-10-yl]-4-(1-methyl-3-indolyl)-1H-pyrrole-2,5-dione.

12. A compound of the formula

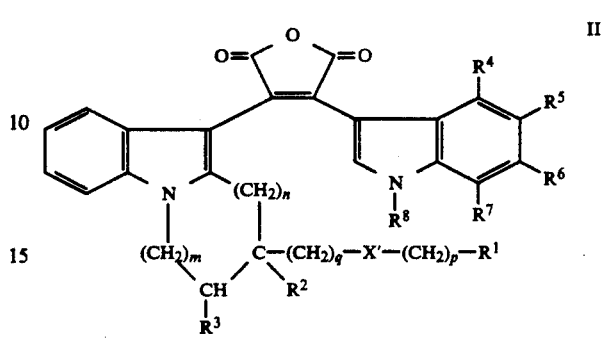

wherein
- $R^1$ and $R^3$ together form a bond and $R^2$ is hydrogen or $R^1$ and $R^2$ together form a bond and $R^3$ is hydrogen;
- $R^4$, $R^5$, $R^6$ and $R^7$ each independently are hydrogen, halogen, $C_{1-7}$ alkyl, halo $C_{1-7}$ alkyl, $C_{1-7}$ alkoxy, nitro, amino, $C_{1-7}$ alkanoylamino, aroylamino, $C_{1-7}$ alkylthio or $C_{1-7}$ alkylsulfonyl;
- $R^8$ is hydrogen, $C_{1-7}$ alkyl or aryl-$C_{1-7}$-alkyl;
- m is 0–2 and n is 1–3, with the proviso that the sum of m and n is 1–3;
- p is 0–4 and q is 0–4, with the proviso that the sum of p and q is 2–4 when X′ is $-N(R^{9'})-$, that the sum of p and q is 1–5 when X′ is $-CHN(R^{10'}, {}^{11'''})-$ and $R^1$ and $R^2$ together form a bond, that the sum of p and q is 0–4 when X′ is $-CHN(R^{10'},R^{11'})-$ and $R^1$ and $R^3$ together form a bond, and that p is 1–4 when X′ is $-N(R^{9'})-$, $R^1$ and $R^3$ together represent a bond and m is O, X′ is $-N(R^{9'})-$ or $-CHN(R^{10'},R^{11'})-$ in which $R^{9'}$, $R^{10'}$ and $R^{11'}$ each are hydrogen, $C_{1-7}$ alkyl, aryl-$C_{1-7}$-alkyl, $C_{1-7}$ alkanoyl, alkoxycarbonyl or aryloxycarbonyl.

13. A pharmaceutical composition comprising an effective amount of a compound of the formula

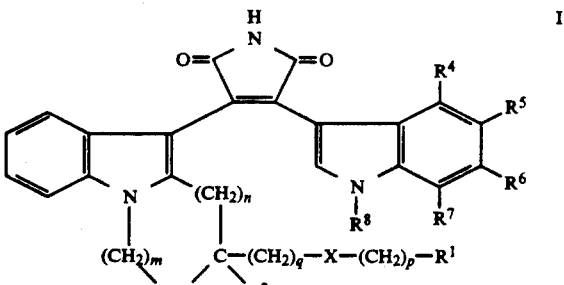

wherein
- $R^1$ and $R^3$ together form a bond and $R^2$ is hydrogen or $R^1$ and $R^2$ together form a bond and $R^3$ is hydrogen;
- $R^4$, $R^5$, $R^6$ and $R^7$ each independently are hydrogen, halogen, $C_{1-7}$ alkyl, halo $C_{1-7}$ alkyl, $C_{1-7}$ alkoxy, nitro, amino, $C_{1-7}$ alkanoylamino, aroylamino, $C_{1-7}$ alkylthio or $C_{1-7}$ alkylsulfonyl;
- $R^8$ is hydrogen, $C_{1-7}$ alkyl or aryl $C_{1-7}$ alkyl;

X is —N($R^9$)— or —CHN($R^{10}$,$R^{11}$)— in which $R^9$, $R^{10}$ and $R^{11}$ each are hydrogen, $C_{1-7}$ alkyl, aryl $C_{1-7}$ alkyl or $C_{1-7}$ alkanoyl;

m is 0–2 and n is 1–3, with the proviso that the sum of m and n is 1–3;

p is 0–4 and q is 0–4, with the proviso that the sum of p and q is 2–4 when X is —N($R^9$)—, that the sum of p and q is 1–5 when X is —CHN($R^{10}$,$R^{11}$)— and $R^1$ and $R^2$ together form a bond, that the sum of p and q is 0–4 when X is —CHN($R^{10}$,$R^{11}$)— and $R^1$ and $R^3$ together form a bond, and that p is 1–4 when X is —N($R^9$)—, $R^1$ and $R^3$ together represent a bond and m is 0, or a pharmaceutically acceptable salt of an acidic compound of formula I with a base or a basic compound of formula I with an acid, and a therapeutically inert carrier.

14. A pharmaceutical composition according to claim 13, wherein $R^1$ and $R^3$ together form a bond and $R^2$ is hydrogen, X is —N($R^9$)— and m, n, p and q each are 1.

15. A pharmaceutical composition according to claim 13, wherein $R^1$ and $R^2$ together form a bond and $R^3$ is hydrogen, X is —N($R^9$)—, m, n and q are 1 and p is 2.

16. A pharmaceutical composition according to claim 13, wherein $R^4$, $R^5$, $R^6$, and $R^7$ each are hydrogen.

17. A pharmaceutical composition according to claim 13, wherein $R^8$ is alkyl $C_{1-7}$.

18. A pharmaceutical composition according to claim 17, wherein $R^8$ is methyl.

19. A pharmaceutical composition according to claim 13, wherein $R^9$ is hydrogen or alkyl $C_{1-7}$.

20. A pharmaceutical composition according to claim 19, wherein $R^9$ is hydrogen or methyl.

21. A pharmaceutical composition according to claim 13, wherein $R^{10}$ and $R^{11}$ each are hydrogen or alkyl $C_{1-7}$.

22. A pharmaceutical composition according to claim 21, wherein $R^{10}$ and $R^{11}$ each are methyl.

23. A pharmaceutical composition according to claim 13, wherein the compound of formula I is selected from the group consisting of 3-[6,7,8,9-Tetrahydrospiro[pyrido[1,2-a]indole-8,3'-pyrrolidin]-10-yl]-4-(1-methyl-3-indolyl)-1H-pyrrole-2,5-dione, cis-3-[2,3,3a,4,11,11a-Hexahydro-2-methyl-1H-pyrrolo[3',4':4,5]pyrido[1,2-a]indol-10-yl]-4-(1-methyl-3-indolyl)-1H-pyrrole-2,5-dione, and trans-3-[2,3,3a,4,11,11a-Hexahydro-2-methyl-1H-pyrrolo[3',4':4,5]pyrido[1,2-a]indol-10-yl]-4-(1-methyl-3-indolyl)-1H-pyrrole-2,5-dione.

24. The compound, trans-3-[2,3,3a,4,11,11a-Hexahydro-2-methyl-1H-pyrrolo[3',4':4,5]pyrido[1,2-a]indol-10-yl]-4-(1-methyl-3-indolyl)-1H-pyrrole-2,5-dione.

* * * * *